United States Patent
Ichinose

(10) Patent No.: US 12,183,450 B2
(45) Date of Patent: Dec. 31, 2024

(54) CONSTRUCTING TRAINED MODELS TO ASSOCIATE OBJECT IN IMAGE WITH DESCRIPTION IN SENTENCE WHERE FEATURE AMOUNT FOR SENTENCE IS DERIVED FROM STRUCTURED INFORMATION

(71) Applicant: FUJIFILM Corporation, Tokyo (JP)

(72) Inventor: Akimichi Ichinose, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 359 days.

(21) Appl. No.: 17/884,525

(22) Filed: Aug. 9, 2022

(65) Prior Publication Data
US 2023/0054096 A1 Feb. 23, 2023

(30) Foreign Application Priority Data

Aug. 17, 2021 (JP) .................. 2021-132919

(51) Int. Cl.
*G16H 30/40* (2018.01)
*G06T 7/00* (2017.01)
(Continued)

(52) U.S. Cl.
CPC ........... *G16H 30/40* (2018.01); *G06T 7/0012* (2013.01); *G06T 7/60* (2013.01); *G06T 7/74* (2017.01);
(Continued)

(58) Field of Classification Search
CPC ........... G06T 7/0012; G06T 7/60; G06T 7/73; G06T 7/74; G06T 7/75;
(Continued)

(56) References Cited

U.S. PATENT DOCUMENTS 11,062,448 B2 * 7/2021 Nakamura ............ G06T 7/0012
11,101,033 B2 * 8/2021 Tao ........................ G16H 15/00
(Continued)

FOREIGN PATENT DOCUMENTS

JP 2020013594 1/2020
WO WO-2021190115 A1 * 9/2021 ........... G06F 16/332
WO WO-2023273572 A1 * 1/2023

OTHER PUBLICATIONS

Barnard, Kobus, et al. "Matching words and pictures." The Journal of Machine Learning Research 3, pp. 1107-1135. (Year: 2003).*

(Continued)

*Primary Examiner* — Scott A Rogers
(74) *Attorney, Agent, or Firm* — JCIPRNET

(57) ABSTRACT

A processor derives a first feature amount for an object included in an image by a first neural network, structures a sentence including description of the object included in the image to derive structured information for the sentence, and derives a second feature amount for the sentence from the structured information by a second neural network. The processor trains the first neural network and the second neural network such that, in a feature space to which the first feature amount and the second feature amount belong, a distance between the derived first feature amount and second feature amount is reduced in a case in which the object included in the image and the object described in the sentence correspond to each other.

17 Claims, 18 Drawing Sheets

(51) Int. Cl.
  *G06T 7/60* (2017.01)
  *G06T 7/73* (2017.01)
(52) U.S. Cl.
  CPC ...... *G06T 7/75* (2017.01); *G06T 2207/10072* (2013.01); *G06T 2207/20081* (2013.01); *G06T 2207/20084* (2013.01); *G06T 2207/30004* (2013.01); *G06T 2207/30064* (2013.01); *G06T 2207/30096* (2013.01)
(58) Field of Classification Search
  CPC . G06T 2207/20084; G06T 2207/30004; G06T 2207/30064; G06T 2207/30096; G06T 2207/10072–10152
  See application file for complete search history.

(56) References Cited

U.S. PATENT DOCUMENTS

| | | | | |
|---|---|---|---|---|
| 11,837,346 | B2* | 12/2023 | Nakamura | G16H 30/40 |
| 2019/0295248 | A1* | 9/2019 | Nakamura | G16H 30/40 |
| 2022/0076796 | A1* | 3/2022 | Momoki | G06T 7/0012 |
| 2022/0366151 | A1* | 11/2022 | Nakamura | A61B 5/055 |
| 2022/0391599 | A1* | 12/2022 | Nakamura | G06F 40/169 |
| 2022/0392595 | A1* | 12/2022 | Ichinose | G16H 30/40 |
| 2022/0392619 | A1* | 12/2022 | Ichinose | G06T 1/00 |
| 2022/0415459 | A1* | 12/2022 | Ichinose | G16H 10/60 |
| 2022/0415461 | A1* | 12/2022 | Momoki | G16H 30/40 |
| 2023/0005178 | A1* | 1/2023 | Liu | G06N 3/0442 |
| 2023/0005580 | A1* | 1/2023 | Momoki | G16H 30/40 |
| 2023/0005601 | A1* | 1/2023 | Nakamura | G16H 15/00 |
| 2023/0030794 | A1* | 2/2023 | Ichinose | G06T 7/0012 |
| 2023/0068201 | A1* | 3/2023 | Ichinose | G06T 7/0012 |
| 2023/0230241 | A1* | 7/2023 | Lure | G16H 50/00 382/128 |
| 2023/0360213 | A1* | 11/2023 | Momoki | G16H 50/20 |
| 2023/0410305 | A1* | 12/2023 | Nakamura | G16H 40/67 |
| 2023/0420096 | A1* | 12/2023 | Nakamura | G06F 40/40 |
| 2024/0046028 | A1* | 2/2024 | Nakamura | G06F 40/166 |
| 2024/0119750 | A1* | 4/2024 | Ichinose | G16H 50/70 |
| 2024/0193932 | A1* | 6/2024 | Ichinose | G06V 10/768 |
| 2024/0203101 | A1* | 6/2024 | Zhang | G06V 20/70 |
| 2024/0266056 | A1* | 8/2024 | Momoki | G16H 50/20 |

OTHER PUBLICATIONS

Karpathy, Andrej, and Li Fei-Fei. "Deep visual-semantic alignments for generating image descriptions." Proceedings of the IEEE conference on computer vision and pattern recognition. (Year: 2015).*
Lan, Hong, and Pufen Zhang. "Learning and integrating multi-level matching features for image-text retrieval." IEEE Signal Processing Letters 29, pp. 374-378. (Year: 2021).*
Pham, Khoi, et al. "Composing object relations and attributes for image-text matching." Proceedings of the IEEE/CVF Conference on Computer Vision and Pattern Recognition. (Year: 2024).*
Wang, Liwei, et al. "Learning two-branch neural networks for image-text matching tasks." IEEE Transactions on Pattern Analysis and Machine Intelligence 41.2, pp. 394-407. (Year: 2018).*
Kuang-Huei Lee et al., "Stacked Cross Attention for Image-Text Matching," arXiv:1803.08024v1, Mar. 2018, pp. 1-23.

* cited by examiner

| EXPRESSION | NORMALIZED EXPRESSION |
|---|---|
| BOUNDARY (POSITION), CLEAR (OPINION+) | BOUNDARY CLEAR (+) |
| BOUNDARY (POSITION), UNCLEAR (OPINION+) | BOUNDARY CLEAR (−) |
| Air-bronchogram (OPINION+) | BRONCHUS TRANSLUCENCY (+) |
| Air-bronchogram (OPINION−) | BRONCHUS TRANSLUCENCY (−) |
| Solid (OPINION+) | SOLID NODULE (+) |
| Solid (OPINION+) | SOLID NODULE (+) |
| PLEURA (POSITION), CLOSE TO (OPINION+) | PLEURA CONTACT (+) |

CONSTRUCTING TRAINED MODELS TO ASSOCIATE OBJECT IN IMAGE WITH DESCRIPTION IN SENTENCE WHERE FEATURE AMOUNT FOR SENTENCE IS DERIVED FROM STRUCTURED INFORMATION

CROSS REFERENCE TO RELATED APPLICATIONS

The present application claims priority under 35 U.S.C. § 119 to Japanese Patent Application No. 2021-132919 filed on Aug. 17, 2021. The above application is hereby expressly incorporated by reference, in its entirety, into the present application.

BACKGROUND

Technical Field

The present disclosure relates to a learning device, a learning method, a learning program, an information processing apparatus, an information processing method, and an information processing program.

Related Art

A method of constructing a feature space to which a feature amount, such as a feature vector, extracted from an image belongs using a trained model that has been subjected to machine learning by deep learning or the like has been proposed. For example, Stacked Cross Attention for Image-Text Matching, Kuang-Huei Lee et al., 21 Mar. 2018, arXiv: 1803.08024 proposes a method of extracting a feature amount from each of an image and a text and estimating a relationship between the image and the text based on the feature amount.

In addition, a method of analyzing text data to acquire word data and specifying an object in an image based on the word data has also been proposed (see JP2020-013594A).

By the way, in a case in which a content of an image is described as a sentence, even in a case in which the contents are the same, an expression method differs depending on a person who describes the image. Therefore, even in a case in which opinion sentences of a medical image are the same, the expression method differs depending on a doctor. For example, in an opinion sentence for a medical image showing an opinion that a solid nodule is present in a section S6 of a right lung, a size thereof is 10 mm, and a boundary is unclear, an expression method differs depending on a doctor who describes the opinion sentence, for example, "A solid nodule is found in a right lung S6. A size is 10 mm. A boundary is slightly unclear.", "A solid nodule having a size of 10 mm is found in a right lung S6. A border is relatively unclear.", and "A solid nodule of φ10 mm is present in a lower right lobe S6. A boundary is slightly unclear." In this way, even in a case in which the contents of the sentence, such as the opinion sentence, are the same, the expression method is different, so that there is a great deal of variations. A large amount of teacher data is required to construct a model that can accurately derive the feature amount from the sentence having various expressions.

However, due to the limited number of sentences, it is difficult to prepare a large amount of teacher data. Therefore, it is difficult to construct a trained model that can associate the image with the sentence with high accuracy.

SUMMARY OF THE INVENTION

The present disclosure has been made in view of the above circumstances, and is to enable association between an image and a sentence with high accuracy.

A learning device according to the present disclosure comprises at least one processor, in which the processor derives a first feature amount for an object included in an image by a first neural network, structures a sentence including description of the object included in the image to derive structured information for the sentence, derives a second feature amount for the sentence from the structured information by a second neural network, and constructs a first derivation model that derives a feature amount for the object included in the image and a second derivation model that derives a feature amount for the sentence including the description of the object by training the first neural network and the second neural network such that, in a feature space to which the first feature amount and the second feature amount belong, a distance between the derived first feature amount and second feature amount is smaller in a case in which the object included in the image and the object described in the sentence correspond to each other than a case in which the object included in the image and the object described in the sentence do not correspond to each other.

It should be noted that, in the learning device according to the present disclosure, the processor may train the first neural network and the second neural network such that, in the feature space, the distance between the derived first feature amount and second feature amount is larger in a case in which the object included in the image and the object described in the sentence do not correspond to each other than a case in which the object included in the image and the object described in the sentence correspond to each other.

In addition, in the learning device according to the present disclosure, the processor may extract one or more unique expressions for the object from the sentence and determine factuality for the unique expression to derive the unique expression and a determination result of the factuality as the structured information.

In addition, in the learning device according to the present disclosure, the unique expression may represent at least one of a position, an opinion, or a size of the object, and the determination result of the factuality may represent any of positivity, negativity, or suspicion for the opinion.

In addition, in the learning device according to the present disclosure, in a case in which a plurality of the unique expressions are extracted, the processor may further derive a relationship between the unique expressions as the structured information.

In addition, in the learning device according to the present disclosure, the relationship may represent whether or not the plurality of unique expressions are related to each other.

In addition, in the learning device according to the present disclosure, the processor may normalize the unique expression and the factuality to derive normalized structured information.

In addition, in the learning device according to the present disclosure, the image may be a medical image, the object included in the image may be a lesion included in the medical image, and the sentence may be an opinion sentence in which an opinion about the lesion is described.

A first information processing apparatus according to the present disclosure comprises at least one processor, in which the processor derives a first feature amount for one or more objects included in a target image by the first derivation model constructed by the learning device according to the present disclosure, structures one or more target sentences including description of the object to derive structured information for the target sentence, derives a second feature amount for the target sentence from the structured information for the target sentence by the second derivation model constructed by the learning device according to the present disclosure, specifies the first feature amount corresponding to the second feature amount based on a distance between the derived first feature amount and second feature amount in a feature space, and displays the object from which the specified first feature amount is derived, in distinction from other regions in the target image.

A second information processing apparatus according to the present disclosure comprises at least one processor, in which the processor receives input of a target sentence including description of an object, structures the target sentence to derive structured information for the target sentence, derives a second feature amount for the input target sentence from the structured information for the target sentence by the second derivation model constructed by the learning device according to the present disclosure, refers to a database in which a first feature amount for one or more objects included in a plurality of reference images, which is derived by the first derivation model constructed by the learning device according to the present disclosure, is associated with each of the reference images, to specify at least one first feature amount corresponding to the second feature amount based on a distance between the first feature amounts for the plurality of reference images and the derived second feature amount in a feature space, and specifies the reference image associated with the specified first feature amount.

It should be noted that, in the first and second information processing apparatuses according to the present disclosure, the processor may give a notification of a unique expression that contributes to association with the first feature amount.

A learning method according to the present disclosure comprising deriving a first feature amount for an object included in an image by a first neural network, structuring a sentence including description of the object included in the image to derive structured information for the sentence, deriving a second feature amount for the sentence from the structured information by a second neural network, and constructing a first derivation model that derives a feature amount for the object included in the image and a second derivation model that derives a feature amount for the sentence including the description of the object by training the first neural network and the second neural network such that, in a feature space to which the first feature amount and the second feature amount belong, a distance between the derived first feature amount and second feature amount is smaller in a case in which the object included in the image and the object described in the sentence correspond to each other than a case in which the object included in the image and the object described in the sentence do not correspond to each other.

A first information processing method according to the present disclosure comprises deriving a first feature amount for one or more objects included in a target image by the first derivation model constructed by the learning device according to the present disclosure, structuring one or more target sentences including description of the object to derive structured information for the target sentence, deriving a second feature amount for the target sentence from the structured information for the target sentence by the second derivation model constructed by the learning device according to the present disclosure, specifying the first feature amount corresponding to the second feature amount based on a distance between the derived first feature amount and second feature amount in a feature space, and displaying the object from which the specified first feature amount is derived, in distinction from other regions in the target image.

A second information processing method according to the present disclosure comprises receiving input of a target sentence including description of an object, structuring the target sentence to derive structured information for the target sentence, deriving a second feature amount for the input target sentence from the structured information for the target sentence by the second derivation model constructed by the learning device according to the present disclosure, referring to a database in which a first feature amount for one or more objects included in a plurality of reference images, which is derived by the first derivation model constructed by the learning device according to the present disclosure, is associated with each of the reference images, to specify at least one first feature amount corresponding to the second feature amount based on a distance between the first feature amounts for the plurality of reference images and the derived second feature amount in a feature space, and specifying the reference image associated with the specified first feature amount.

It should be noted that the learning method, and the first and second information processing methods according to the present disclosure may be provided as a program to be executed by a computer.

According to the present disclosure, it is possible to associate the image with the sentence with a high accuracy.

DETAILED DESCRIPTION

Figure 1:
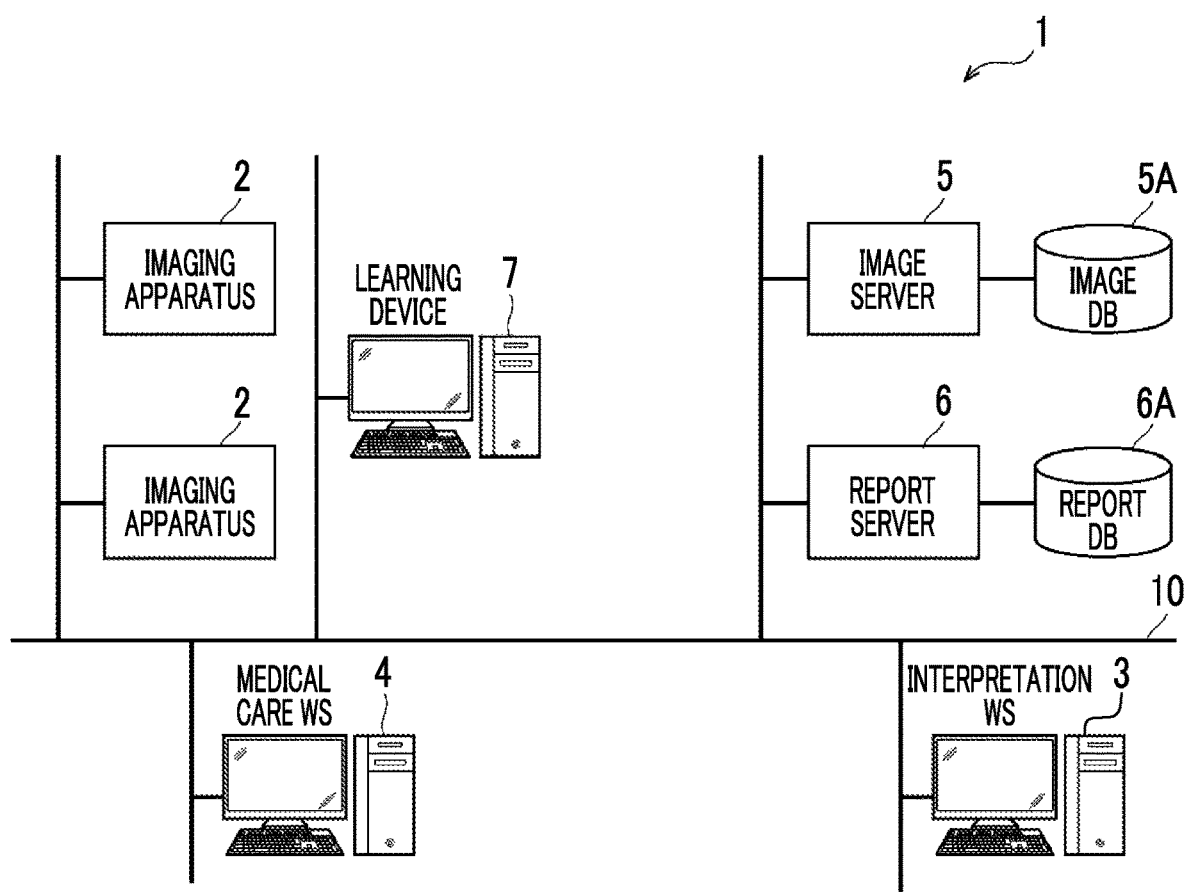
FIG. 1 is a diagram showing a schematic configuration of a medical information system to which a learning device and an information processing apparatus according to a first embodiment of the present disclosure are applied.

In the following, embodiments of the present disclosure will be described with reference to the drawings. First, a configuration of a medical information system to which a learning device and an information processing apparatus according to a first embodiment of the present disclosure are applied will be described. FIG. 1 is a diagram showing a schematic configuration of a medical information system 1. The medical information system 1 shown in FIG. 1 is a system that performs imaging of an examination target part of a patient who is a subject, the storage of a medical image acquired by imaging, the interpretation of the medical image and the creation of an interpretation report by an interpreter, and viewing of the interpretation report and the detailed observation of the medical image of an interpretation target by the doctor of the medical care department which is a request source, based on an examination order from a doctor of a medical care department by using a known ordering system.

As shown in FIG. 1, the medical information system 1 has a configuration in which a plurality of imaging apparatuses 2, a plurality of interpretation work stations (WSs) 3, a medical care WS 4, an image server 5, an image database (DB) 5A, a report server 6, a report DB 6A, and a learning device 7 are connected via a wired or wireless network 10 to be able to communicate with each other.

Each device is a computer on which an application program for functioning as a component of the medical information system 1 is installed. The application program is recorded in a recording medium, such as a digital versatile disc (DVD) and a compact disc read only memory (CD-ROM), is distributed, and is installed in the computer from the recording medium. Alternatively, the application program is stored in a storage device of a server computer connected to the network 10 or in a network storage in a state of being accessible from the outside, and is downloaded and installed in the computer in response to the request.

The imaging apparatus 2 is an apparatus (modality) that generates the medical image representing a diagnosis target part by imaging the diagnosis target part of the patient. Specifically, the imaging apparatus 2 is a simple X-ray imaging apparatus, a CT apparatus, an MRI apparatus, a positron emission tomography (PET) apparatus, and the like. The medical image generated by the imaging apparatus 2 is transmitted to the image server 5 and is then stored in the image DB 5A.

The interpretation WS 3 is a computer used by, for example, the interpreter of a radiology department to perform the interpretation of the medical image and the creation of the interpretation report, and encompasses the information processing apparatus (details will be described below) according to the present embodiment. In the interpretation WS 3, a viewing request for the medical image to the image server 5, various types of image processing for the medical image received from the image server 5, displaying of the medical image, and an input reception of an opinion sentence relating to the medical image are performed. In addition, in the interpretation WS 3, analysis processing of the medical image, support for creating the interpretation report based on the analysis result, a registration request and a viewing request for the interpretation report to the report server 6, and displaying of the interpretation report received from the report server 6 are performed. These types of processing are performed by the interpretation WS 3 executing a software program for each processing.

The medical care WS 4 is a computer used by the doctor of the medical care department to perform the detailed observation of the image, viewing of the interpretation report, the creation of an electronic medical record, and the like, and is composed of a processing apparatus, a display device, such as a display, and an input device, such as a keyboard and a mouse. In the medical care WS 4, the viewing request for the image to the image server 5, displaying of the image received from the image server 5, the viewing request for the interpretation report to the report server 6, and displaying of the interpretation report received from the report server 6 are performed. These types of processing are performed by the medical care WS 4 executing a software program for each processing.

The image server 5 is a server in which a software program providing a function of a database management system (DBMS) to a general-purpose computer is installed. In addition, the image server 5 comprises a storage constituting the image DB 5A. This storage may be a hard disk device connected to the image server 5 by a data bus, or may be a disk device connected to a network attached storage (NAS) and a storage area network (SAN) connected to the network 10. In addition, in a case in which the image server 5 receives the registration request of the medical image from the imaging apparatus 2, the image server 5 arranges the medical image in a format for a database and registers the arranged medical image in the image DB 5A.

In the image DB 5A, image data of the medical image acquired in the imaging apparatus 2 and accessory information are registered. The accessory information includes, for example, an image identification (ID) for identifying an individual medical image, a patient ID for identifying the patient, an examination ID for identifying the examination, a unique identification (UID) assigned to each medical image, an examination date and an examination time at which each medical image is generated, a type of imaging apparatus used in the examination to acquire each medical image, patient information, such as a name, an age, and a gender of the patient, an examination part (imaging part), imaging information (imaging protocol, imaging sequence, imaging method, imaging condition, use of contrast agent, and the like), and information, such as a series number or a collection number in a case in which a plurality of medical images are acquired in one examination. In addition, in the present embodiment, a first feature amount of the medical image derived as described below in the interpretation WS 3 is registered in the image DB 5A in association with the medical image.

In addition, in a case in which the viewing request from the interpretation WS 3 and the medical care WS 4 is received via the network 10, the image server 5 searches for the medical image registered in the image DB 5A and transmits the searched medical image to the interpretation WS 3 and the medical care WS 4 that are request sources.

The report server 6 incorporates the software program that provides the function of the database management system to the general-purpose computer. In a case in which the registration request for the interpretation report from the interpretation WS 3 is received, the report server 6 arranges the interpretation report in the format for a database, and registers the arranged interpretation report in the report DB 6A.

In the report DB 6A, a large number of interpretation reports including the opinion sentences created by the interpreter using the interpretation WS 3 are registered. The interpretation report may include, for example, information, such as the medical image of the interpretation target, the image ID for identifying the medical image, an interpreter ID for identifying the interpreter who performs the interpretation, a lesion name, positional information of the lesion, and a property of the lesion. In the present embodiment, the interpretation report and one or more medical images for which the interpretation report is created are associated with each other and registered in the report DB 6A.

In addition, in a case in which the viewing request for the interpretation report is received from the interpretation WS 3 and the medical care WS 4 via the network 10, the report server 6 searches for the interpretation report registered in the report DB 6A, and transmits the searched interpretation report to the interpretation WS 3 and the medical care WS 4, which are the request sources.

The network 10 is a wired or wireless local area network that connects various devices in a hospital. In a case in which the interpretation WS 3 is installed in another hospital or clinic, the network 10 may have a configuration in which the local area networks of respective hospitals are connected to each other via the Internet or a dedicated circuit.

Figure 2:
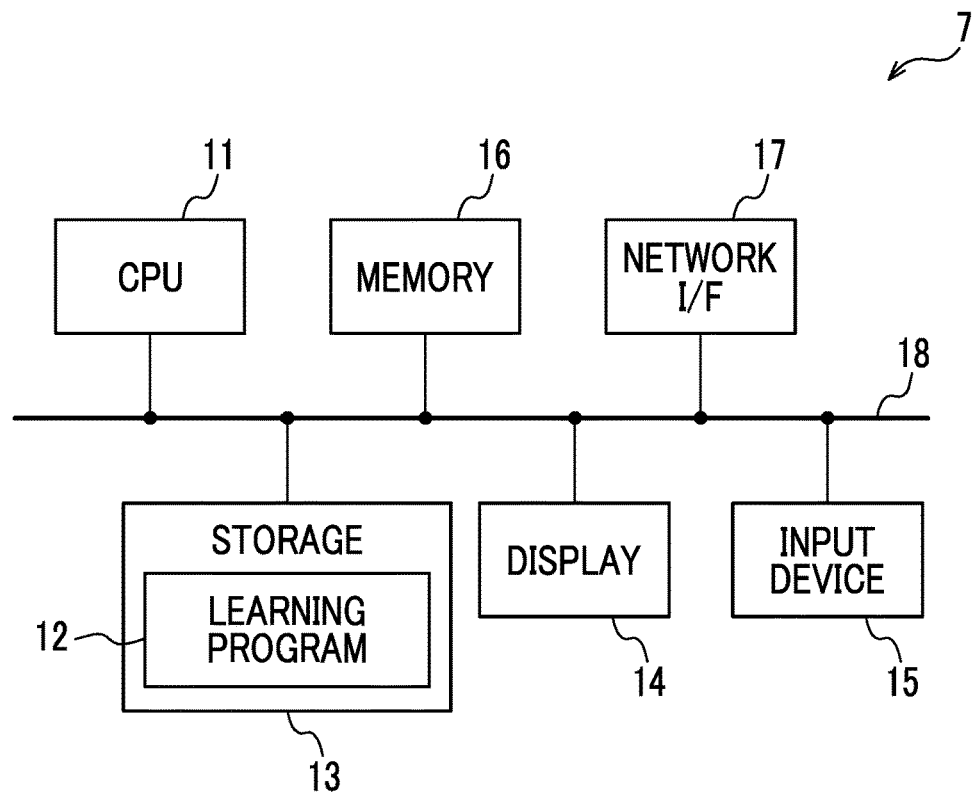
FIG. 2 is a diagram showing a schematic configuration of the learning device according to the first embodiment.

Next, the learning device 7 will be described. A hardware configuration of the learning device 7 according to the first embodiment will be described with reference to FIG. 2. As shown in FIG. 2, the learning device 7 includes a central processing unit (CPU) 11, a non-volatile storage 13, and a memory 16 as a temporary storage region. In addition, the learning device 7 includes a display 14, such as a liquid crystal display, an input device 15 consisting of a pointing device, such as the keyboard and the mouse, and a network interface (I/F) 17 connected to the network 10. The CPU 11, the storage 13, the display 14, the input device 15, the memory 16, and the network I/F 17 are connected to a bus 18. It should be noted that the CPU 11 is an example of a processor according to the present disclosure.

The storage 13 is realized by a hard disk drive (HDD), a solid state drive (SSD), and a flash memory, and the like. The storage 13 as a storage medium stores a learning program 12. The CPU 11 reads out the learning program 12 from the storage 13, develops the read-out learning program 12 in the memory 16, and executes the developed learning program 12.

Figure 3:
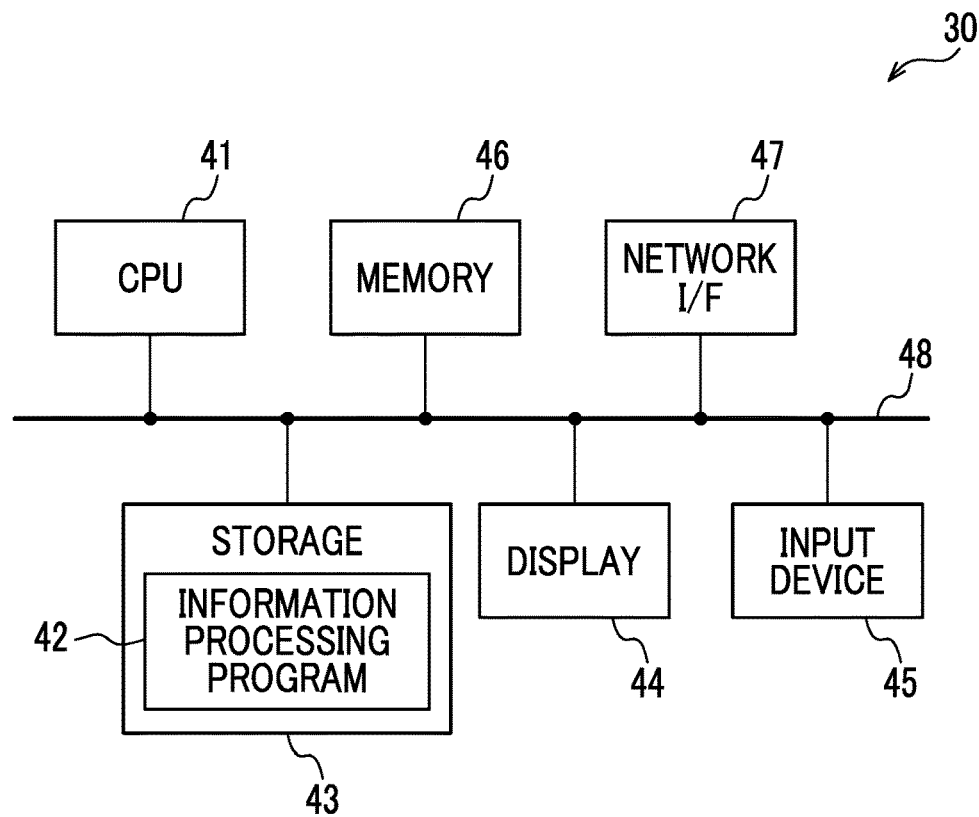
FIG. 3 is a diagram showing a schematic configuration of the information processing apparatus according to the first embodiment.

Next, an information processing apparatus 30 according to the first embodiment encompassed in the interpretation WS 3 will be described. First, a hardware configuration of the information processing apparatus 30 according to the present embodiment will be described with reference to FIG. 3. As shown in FIG. 3, the information processing apparatus 30 includes a CPU 41, a non-volatile storage 43, and a memory 46 as a temporary storage region. In addition, the information processing apparatus 30 includes a display 44, such as the liquid crystal display, an input device 45 consisting of the pointing device, such as the keyboard and the mouse, and a network I/F 47 connected to the network 10. The CPU 41, the storage 43, the display 44, the input device 45, the memory 46, and the network I/F 47 are connected to a bus 48. It should be noted that the CPU 41 is an example of the processor according to the present disclosure.

Similar to the storage 13, the storage 43 is realized by the HDD, the SSD, the flash memory, and the like. An information processing program 42 is stored in the storage 43 as the storage medium. The CPU 41 reads out the information processing program 42 from the storage 43, develops the read-out information processing program 42 in the memory 46, and executes the developed information processing program 42.

Figure 4:
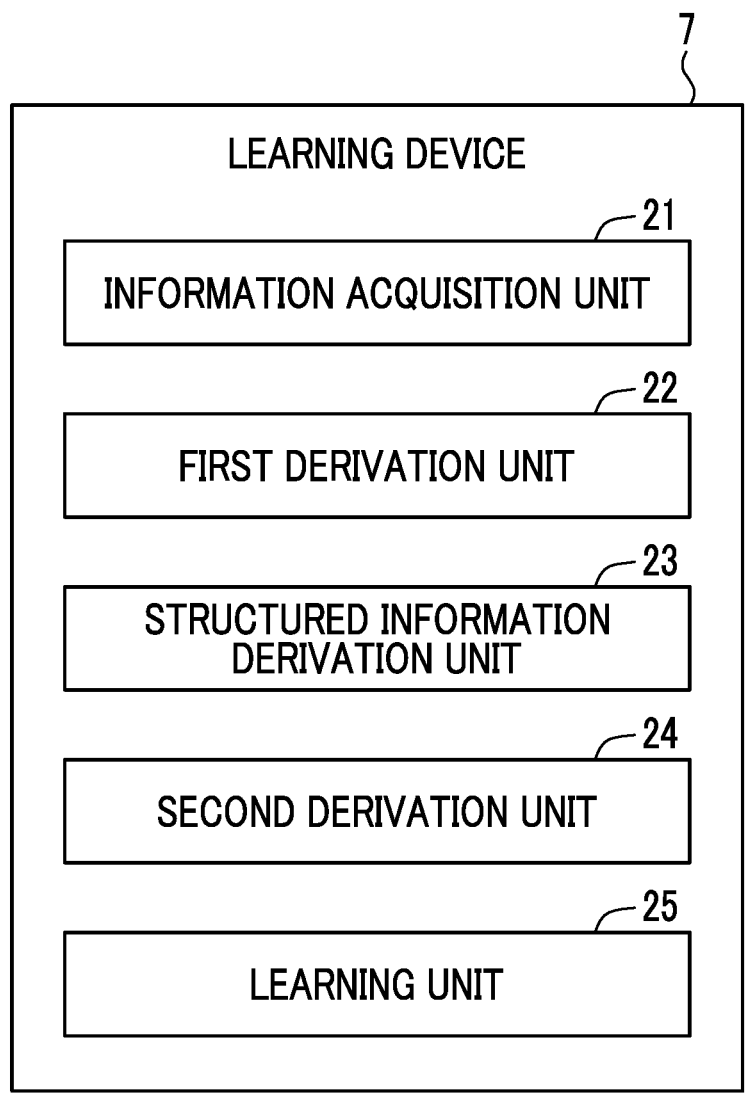
FIG. 4 is a functional configuration diagram of the learning device according to the first embodiment.

Then, a functional configuration of the learning device according to the first embodiment will be described. FIG. 4 is a diagram showing the functional configuration of the learning device according to the first embodiment. As shown in FIG. 4, the learning device 7 comprises an information acquisition unit 21, a first derivation unit 22, a structured information derivation unit 23, a second derivation unit 24, and a learning unit 25. Moreover, by the CPU 11 executing the learning program 12, the CPU 11 functions as the information acquisition unit 21, the first derivation unit 22, the structured information derivation unit 23, the second derivation unit 24 and the learning unit 25.

Figure 5:
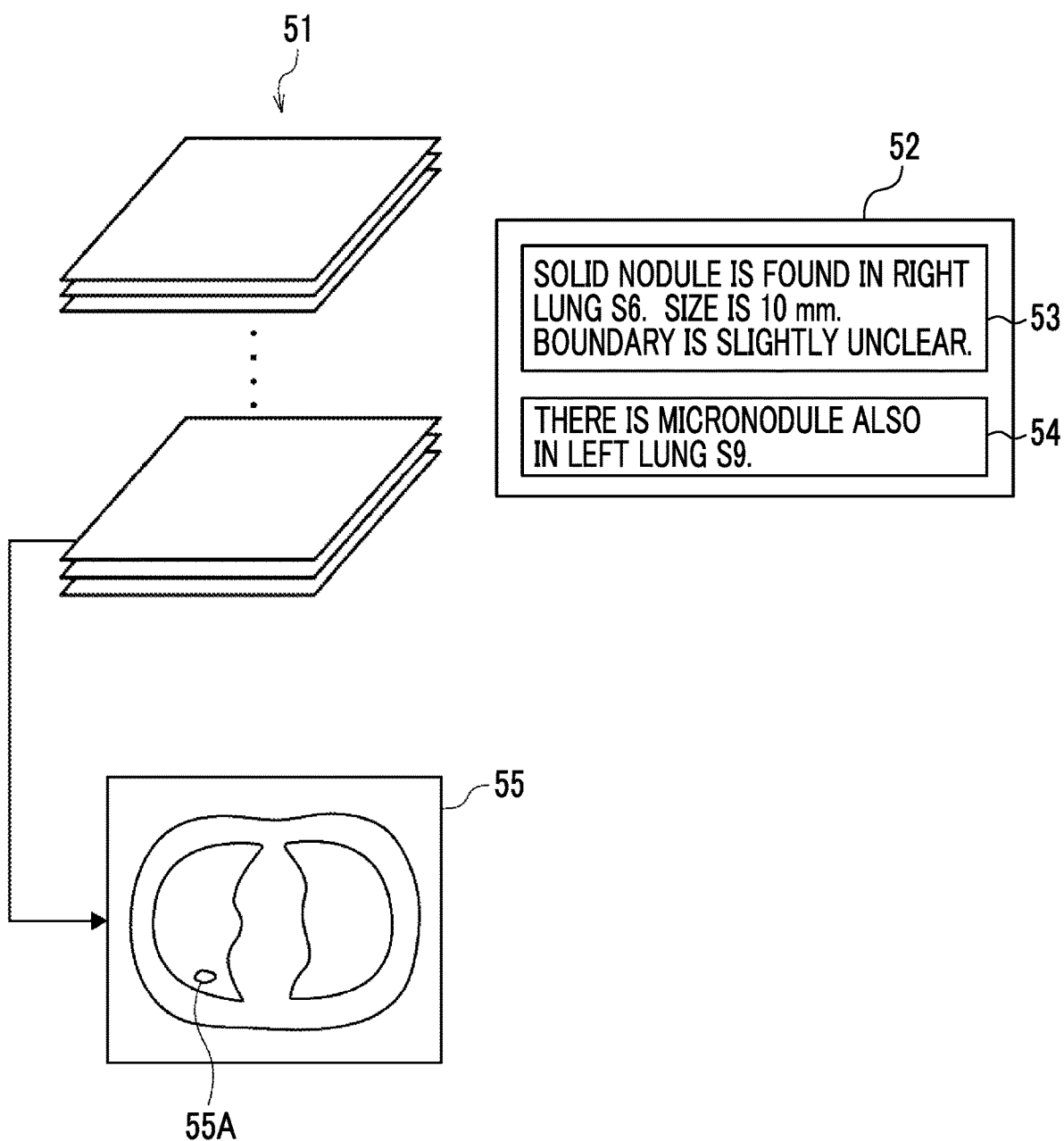
FIG. 5 is a diagram showing examples of a medical image and an interpretation report.

The information acquisition unit 21 acquires the medical image and the interpretation report about the medical image from the image server 5 and the report server 6, respectively, via the network I/F 17. The medical image and the interpretation report are used to train first and second neural networks described below. FIG. 5 is a diagram showing examples of the medical image and the interpretation report. As shown in FIG. 5, a medical image 51 is a three-dimensional image consisting of a plurality of tomographic images. In the present embodiment, the medical image 51 is a CT image of a chest of a human body. In addition, as shown in FIG. 5, the plurality of tomographic images include a tomographic image 55 including the lesion in the right lung S6 as an object 55A.

In addition, as shown in FIG. 5, an interpretation report 52 includes opinion sentences 53 and 54. The opinion sentences 53 and 54 include description of the object or the lesion included in the medical image 51. The opinion sentence 53 shown in FIG. 5 includes the description of "A solid nodule is found in the right lung S6. A size is 10 mm. A boundary is slightly unclear." In addition, the opinion sentence 54 includes the description of "There is a micronodule also in the left lung S9."

Among the two opinion sentences 53 and 54 shown in FIG. 5, the opinion sentence 53 is generated as a result of interpreting the tomographic image 55 included in the medical image 51. Therefore, the tomographic image 55 corresponds to the opinion sentence 53. The opinion sentence 54 is generated as a result of interpreting a tomographic image other than the tomographic image 55 in the medical image 51. Therefore, the tomographic image 55 and the opinion sentence 54 do not correspond to each other.

Figure 6:
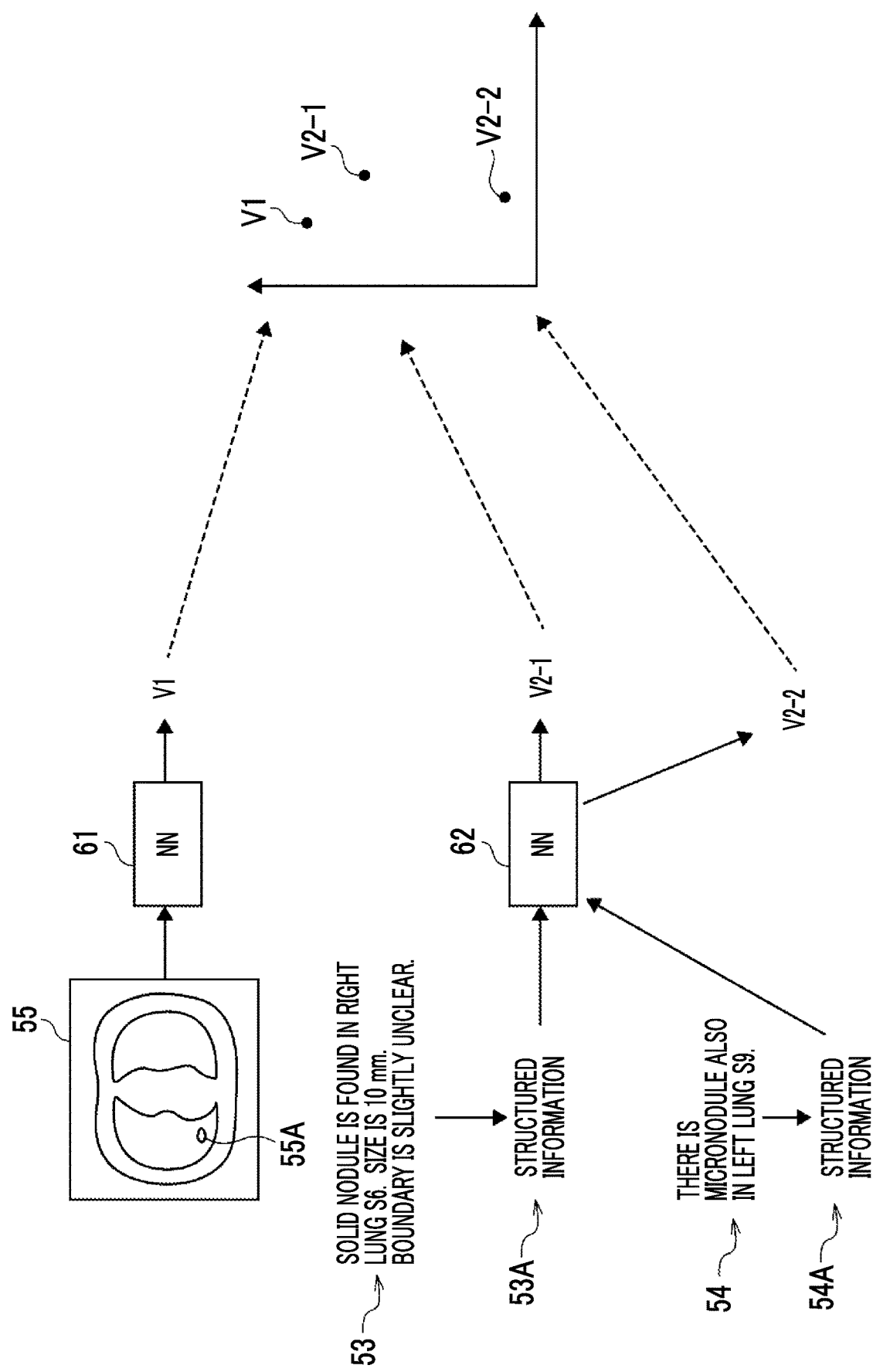
FIG. 6 is a diagram schematically showing processing performed by a first derivation unit, a structured information derivation unit, a second derivation unit, and a learning unit in the first embodiment.

The first derivation unit 22 derives the first feature amount for one or more objects included in the medical image by using a first neural network (NN) 61 to construct a first derivation model that derives the feature amount for the object included in the medical image. In the present embodiment, the first neural network 61 is a convolutional neural network (CNN), but is not limited to this. As shown in FIG. 6, the first derivation unit 22 inputs an image, such as the medical image including the object, such as the lesion, to the first neural network 61. The first neural network 61 extracts an object, such as the lesion, included in the image, and derives a feature vector of the object as a first feature amount V1.

Figures 7, 8:
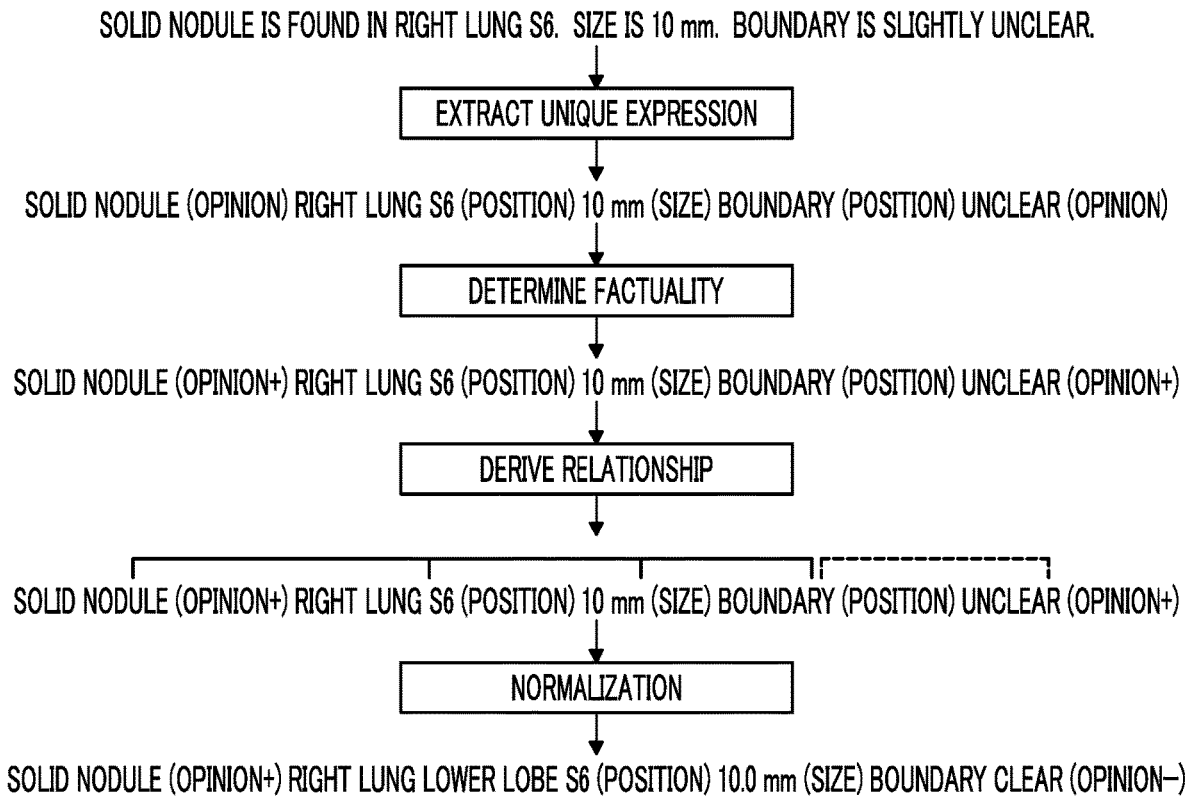
FIG. 7 is a diagram for describing structuring.
FIG. 8 is a diagram showing an example of a list in which a synonymous expression and a normalized expression are associated with each other.

The structured information derivation unit 23 derives structured information about the opinion sentences 53 and 54 by structuring the opinion sentences 53 and 54. FIG. 7 is a diagram showing processing performed by the structured information derivation unit 23. In the following, the structuring of the opinion sentence 53 will be described, but the structured information need only be derived in the same manner for the opinion sentence 54. First, the structured information derivation unit 23 derives a unique expression related to the object from the opinion sentence 53. The unique expression is an example of the structured information. The unique expression represents at least one of a position, an opinion, or a size of the object included in the opinion sentence 53. In the present embodiment, all of the position, the opinion, and the size of the object included in the opinion sentence 53 are derived as the unique expression. Therefore, the structured information derivation unit 23 derives "right lung S6", "solid nodule", "10 mm", "boundary", and "unclear" as the unique expression. It should be noted that "right lung S6" is a unique expression that represents the position, "solid nodule" is a unique expression that represents the opinion, "10 mm" is a unique expression that represents the size, "boundary" is a unique expression that represents the position, and "unclear" is a unique expression that represents the opinion. In the following, the unique expression derived from the opinion sentence 53 is referred to as "right lung S6 (position)", "solid nodule (opinion)", "10 mm (size)", "boundary (position)", and "unclear (opinion)".

In addition, the structured information derivation unit 23 determines the factuality of the derived unique expression. Specifically, the structured information derivation unit 23 determines whether the unique expression of the opinion represents negativity, positivity, or suspicion to derive a determination result. In the present embodiment, the unique expressions of the opinion are "solid nodule" and "unclear", both of which represent the positivity. Therefore, the structured information derivation unit 23 determines that the factuality of each of "solid nodule" and "unclear" represents the positivity. In FIG. 7, the positivity is indicated by adding a + sign. In addition, in a case of the negativity, a − sign need only be added, and in a case of the suspicion, a ± sign need only be added. The determination result of the factuality is an example of the structured information.

In addition, the structured information derivation unit 23 derives a relationship between a plurality of unique expressions. The relationship is an example of the structured information. It should be noted that, in the first embodiment, the relationship is not used in the processing described below, but since the relationship is one of the structured information, the relationship will also be described here. The relationship represents whether or not the unique expressions are related to each other. For example, the unique expression of "solid nodule (opinion+)" that represents the opinion about a typical lesion among the unique expressions is related to the unique expression of "10 mm (size)" that represents the size, the unique expression of "right lung S6 (position)" that represents the position, and the unique expression of "unclear (opinion+)" that represents the opinion, but is not related to the unique expression of "boundary (position)" that represents the position. In addition, the unique expression of "boundary (position)" that represents the position is related to the unique expression of "unclear (opinion+)" that represents the opinion.

It should be noted that the relationship need only be derived by referring to a table in which the presence or absence of the relationship between a large number of unique expressions is defined in advance. In addition, the relationship may be derived using a derivation model constructed by performing machine learning to output the presence or absence of the relationship between the unique expressions. In addition, the lesion described in the unique expression may be specified as a keyword, and all the unique expressions that modify the keyword may be specified as the related unique expressions.

Further, the structured information derivation unit 23 normalizes the unique expression and the factuality to derive the normalized structured information. The normalization in the present embodiment is converting the expressions which are synonymous but variable into one fixed expression. For example, "right lung S6" and "right lung lower lobe S6" are synonymous, but the expressions are different. In addition, "10 mm" and "10.0 mm" are synonymous, but the expressions are different. In addition, a combination of "boundary" and "unclear (+)" is synonymous with the expression of "boundary clear (—)" in which the factuality of "boundary clear" represents the negativity, but the expression is different.

For example, in the present embodiment, a list in which synonymous expressions and normalized expressions are associated with each other for a large number of unique expressions and the factuality is prepared in advance and stored in the storage 13. FIG. 8 is a diagram showing an example of a list in which the synonymous expression and the normalized expression are associated with each other. Moreover, the structured information derivation unit 23 normalizes the unique expression and the factuality with reference to a list 59. As a result, the structured information derivation unit 23 derives the normalized structured information of "right lung lower lobe S6 (position)", "solid nodule (opinion+)", "10.0 mm (size)", and "boundary clear (opinion−)" from the opinion sentence 53. On the other hand, the structured information derivation unit 23 derives the normalized structured information of "left lung lower lobe S9 (position)", "micro (size)", and "nodule (opinion+)" from the opinion sentence 54.

Figure 9:
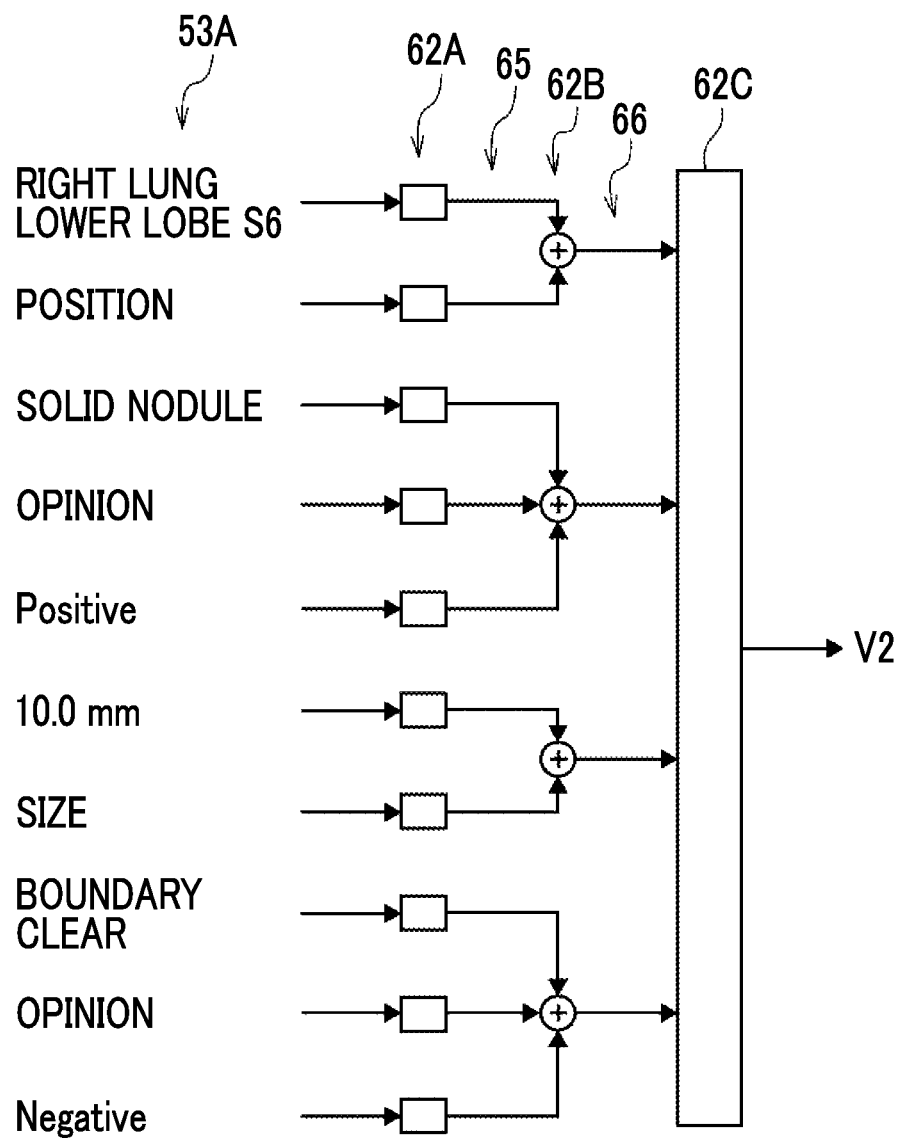
FIG. 9 is a diagram schematically showing a second neural network.

The second derivation unit 24 derives, from the structured information derived by the structured information derivation unit 23, a second feature amount for a sentence including the description of the object by using a second neural network (NN) 62 to construct a second derivation model that derives the feature amount for the sentence including the description of the object. FIG. 9 is a diagram schematically showing the second neural network 62. As shown in FIG. 9, the second neural network 62 includes an embedding layer 62A, an addition mechanism 62B, and a transformer 62C. The second derivation unit 24 divides the input structured information into the unique expression, the type of the unique expression, and the determination result of the factuality, and inputs the divided structured information to the embedding layer 62A. The embedding layer 62A outputs a feature vector 65 for the unique expression, the type of the unique expression, and the determination result of the factuality.

The addition mechanism 62B adds the feature vector 65 for each structured information, and derives a feature vector 66 for each structured information.

The transformer is proposed, for example, in "Vaswani, Ashish, et al. "Attention is all you need." Advances in neural information processing systems. 2017." The transformer 62C derives a similarity between the feature vectors 66, integrates the feature vectors 66 by repeating processing of adding the feature vectors 66 by a weight corresponding to the derived similarity, and outputs the feature vector of the structured information input to the second neural network 62, that is, the feature vector for the opinion sentence 53 input to the structured information derivation unit 23 as a second feature amount V2.

Figure 10:
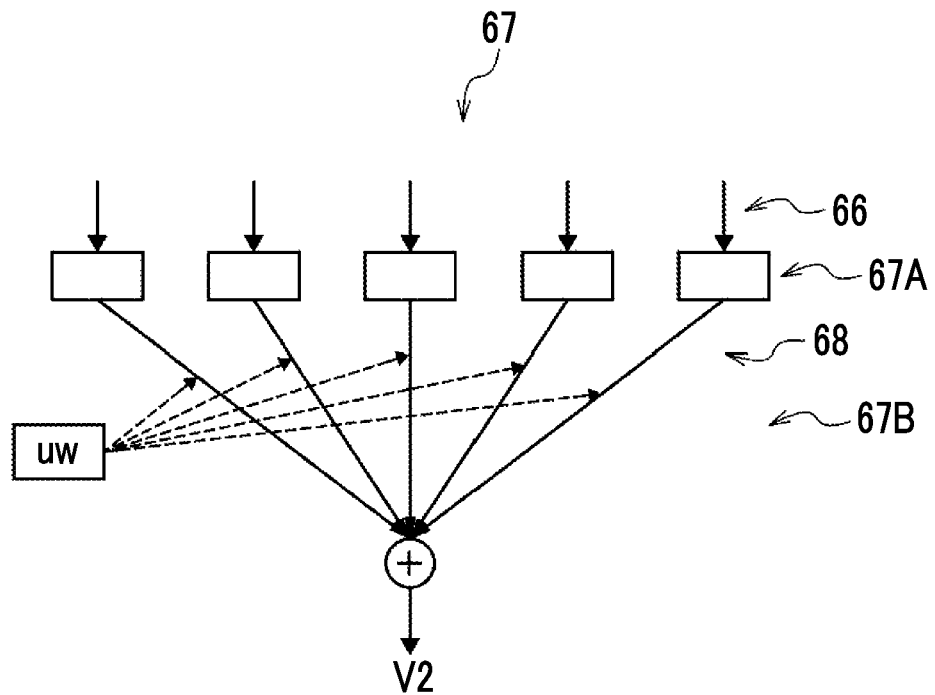
FIG. 10 is a diagram schematically showing a network structure in which an RNN and an attention mechanism are combined.

It should be noted that, as a mechanism on a subsequent stage of the addition mechanism 62B, a network structure may be used in which an RNN and an attention mechanism are combined, instead of the transformer 62C. FIG. 10 is a diagram schematically showing the network structure in which the RNN and the attention mechanism are combined. A network structure 67 shown in FIG. 10 includes a recurrent neural network layer (hereinafter referred to as an RNN layer) 67A and an attention mechanism 67B.

The RNN layer 67A outputs a feature vector 68 in consideration of the context of the feature vector 66 output by the addition mechanism 62B. The attention mechanism 67B derives an inner product of a vector uw derived by learning in advance and each feature vector 68 as a weighting coefficient w. The vector uw is trained such that a greater weight is given to the unique expression having a larger degree of contribution in deriving the output second feature amount V2. Moreover, the attention mechanism 67B derives the second feature amount V2 by weighting and adding the feature vector 68 with the derived weighting coefficient w.

Here, in the first embodiment, as shown in FIG. 6, the structured information 53A is derived from the opinion sentence 53 of "A solid nodule is found in the right lung S6. A size is 10 mm. A boundary is slightly unclear." Then, a second feature amount V2-1 is acquired from the structured information 53A by the second neural network 62. In addition, the structured information 54A is derived from the opinion sentence 54 of "There is a micronodule also in the left lung S9." Then, a second feature amount V2-2 is acquired from the structured information 54A by the second neural network 62.

The learning unit 25 trains the first neural network 61 and the second neural network 62 such that, in a feature space to which the first feature amount V1 and the second feature amount V2 belong, a distance between the derived first feature amount V1 and second feature amount V2 is reduced in a case in which the object included in the image and the object described in the sentence correspond to each other.

Therefore, the learning unit 25 plots the first feature amount V1 and the second feature amount V2 in the feature space defined by the first feature amount V1 and the second feature amount V2. Moreover, the learning unit 25 derives the distance between the first feature amount V1 and the second feature amount V2 in the feature space. Here, since the first feature amount V1 and the second feature amount V2 are n-dimensional vectors, the feature space is also n-dimensional. It should be noted that, in FIG. 6, for the sake of description, the first feature amount V1 and the second feature amount V2 are two-dimensional, and a state in which the first feature amount V1 and the second feature amount V2 (V2-1 and V2-2) are plotted in the two-dimensional feature space is shown.

Here, the tomographic image 55 shown in FIG. 6 corresponds to the opinion sentence 53, but does not correspond to the opinion sentence 54. Therefore, in the feature space, the learning unit 25 trains the first neural network 61 and the second neural network 62 such that the first feature amount V1 and the second feature amount V2-1 get close to each other, and the first feature amount V1 and the second feature amount V2-2 are separated from each other.

Figure 11:
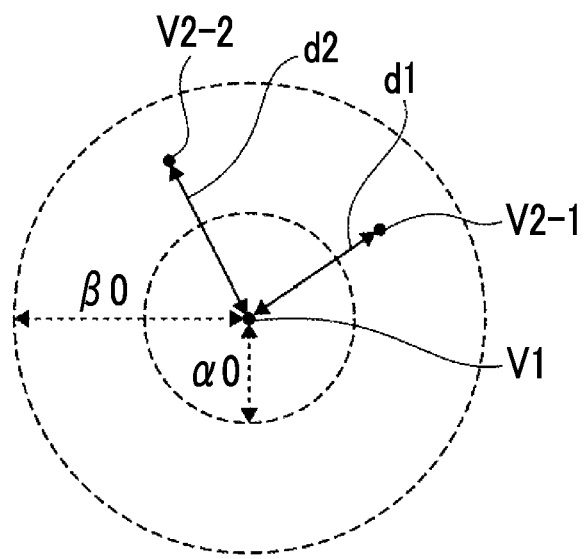
FIG. 11 is a diagram for describing the derivation of a loss.

Therefore, the learning unit 25 derives the distance between the first feature amount V1 and the second feature amount V2 in the feature space. As the distance, any distance, such as a Euclidean distance and the Mahalanobis distance, can be used. Moreover, a loss used in learning is derived based on the distance. FIG. 11 is a diagram for describing the derivation of the loss. First, the learning unit 25 calculates a distance d1 in the feature space for the first feature amount V1 and the second feature amount V2-1 which correspond to each other. Moreover, the distance d1 is compared with a predetermined threshold value $\alpha 0$ to derive a loss L1 based on Expression (1).

That is, in a case in which the distance d1 between the first feature amount V1 and the second feature amount V2-1 is larger than the threshold value $\alpha 0$, the loss L1, which is for training the first and second neural networks 61 and 62 such that the distance of the second feature amount V2-1 from the first feature amount V1 is smaller than the threshold value $\alpha 0$, is calculated by $d1 - \alpha 0$. On the other hand, in a case in which the distance d1 between the first feature amount V1 and the second feature amount V2-1 is equal to or smaller than the threshold value $\alpha 0$, it is not necessary to reduce the distance d1 between the first feature amount V1 and the second feature amount V2-1, so that the loss L1 is set to 0.

$$L1 = d1 - \alpha 0 \, (d1 > \alpha 0)$$

$$L1 = 0 \, (d1 \leq \alpha 0) \qquad (1)$$

On the other hand, the learning unit 25 calculates a distance d2 in the feature space for the first feature amount V1 and the second feature amount V2-2 which do not correspond to each other. Moreover, the distance d2 is compared with a predetermined threshold value $\beta 0$ to derive a loss L2 based on Expression (2).

That is, in a case in which the distance d2 between the first feature amount V1 and the second feature amount V2-2 is smaller than the threshold value $\beta 0$, the loss L2, which is for training the first and second neural networks 61 and 62 such that the distance of the second feature amount V2-2 from the first feature amount V1 is larger than the threshold value $\beta 0$, is calculated by $\beta 0 - d2$. On the other hand, in a case in which the distance d2 between the first feature amount V1 and the second feature amount V2-2 is equal to or larger than the threshold value $\beta 0$, it is not necessary to increase the distance d2 between the first feature amount V1 and the second feature amount V2-2, so that the loss L2 is set to 0.

$$L2 = \beta 0 - d2 \, (d2 < \beta 0)$$

$$L2 = 0 \, (d2 \geq \beta 0) \qquad (2)$$

The learning unit 25 trains the first neural network 61 and the second neural network 62 based on the derived losses L1 and L2. That is, in a case of $d1 > \alpha 0$ and in a case of $d2 < \beta 0$, a kernel coefficient used in the weights and convolutions of the bonding between the layers constituting each of the first neural network 61 and the second neural network 62 is trained such that the losses L1 and L2 are reduced.

Moreover, the learning unit 25 repeatedly performs learning until the loss L1 is equal to or smaller than the predetermined threshold value and the loss L2 is equal to or smaller than the threshold value. It should be noted that it is preferable that the learning unit 25 repeatedly perform learning until the loss L1 is continuously equal to or smaller than the threshold value a predetermined number of times and the loss L2 is continuously equal to or smaller than the threshold value a predetermined number of times. As a result, the first derivation model and the second derivation model that derive the first feature amount V1 and the second feature amount V2 are constructed such that, in a case in which the image and the sentence correspond to each other, the distance in the feature space is smaller than a case in which the image and the sentence do not correspond to each other, and in a case in which the image and the sentence do not correspond to each other, the distance in the feature space is larger than a case in which the image and the sentence correspond to each other. It should be noted that the learning unit 25 may repeatedly perform learning a predetermined number of times.

The first derivation model and the second derivation model constructed in this way are transmitted to the interpretation WS 3 and used in the information processing apparatus according to the first embodiment.

Figure 12:
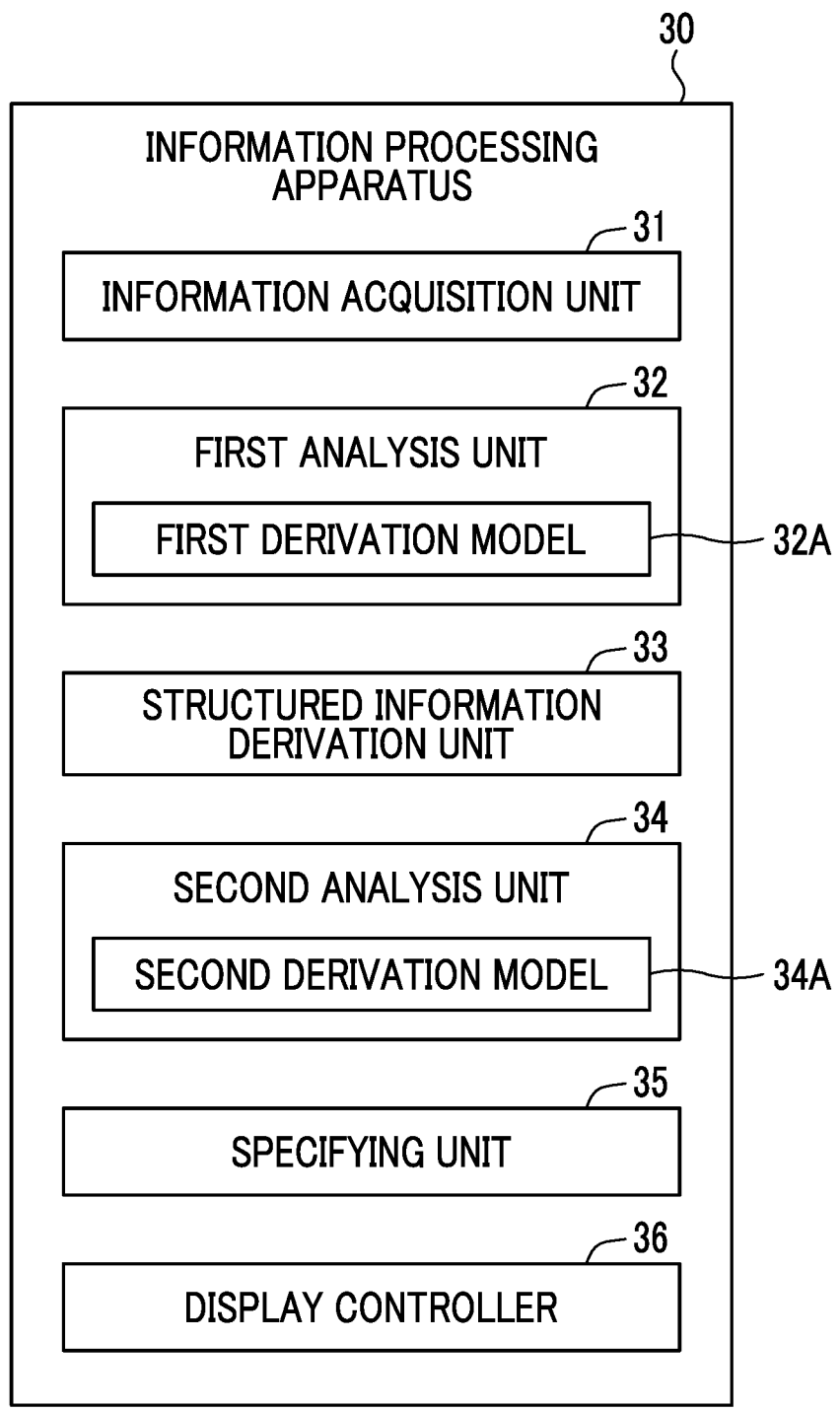
FIG. 12 is a functional configuration diagram of the information processing apparatus according to the first embodiment.

Then, a functional configuration of the information processing apparatus according to the first embodiment will be described. FIG. 12 is a diagram showing the functional configuration of the information processing apparatus according to the first embodiment. As shown in FIG. 12, the information processing apparatus 30 comprises an information acquisition unit 31, a first analysis unit 32, a structured information derivation unit 33, a second analysis unit 34, a specifying unit 35, and a display controller 36. Moreover, by the CPU 41 executing the information processing program 42, the CPU 41 functions as the information acquisition unit 31, the first analysis unit 32, the structured information derivation unit 33, the second analysis unit 34, the specifying unit 35, and the display controller 36.

The information acquisition unit 31 acquires a target medical image G0, which is the interpretation target, from the image server 5 in response to an instruction from the input device 45 by the interpreter who is an operator.

The first analysis unit 32 analyzes the target medical image G0 using a first derivation model 32A constructed by the learning device 7 described above to derive the first feature amount V1 for the object, such as the lesion, included in the target medical image G0. It should be noted that, in the present embodiment, the target medical image G0 includes two objects, and the first feature amounts V1-1 and V1-2 are derived for each of the two objects.

Here, in the information processing apparatus 30 according to the first embodiment, the interpretation report is generated by the interpreter interpreting the target medical image G0 in the interpretation WS 3 and inputting the opinion sentence including an interpretation result by using the input device 45.

The structured information derivation unit 33 derives the structured information from the input opinion sentence. The derivation of the structured information is performed in the same manner as in the structured information derivation unit 23 of the learning device 7.

The second analysis unit 34 derives the second feature amount V2 for the input opinion sentence by analyzing the structured information derived from the input opinion sentence using a second derivation model 34A constructed by the learning device 7 described above.

Figure 13:
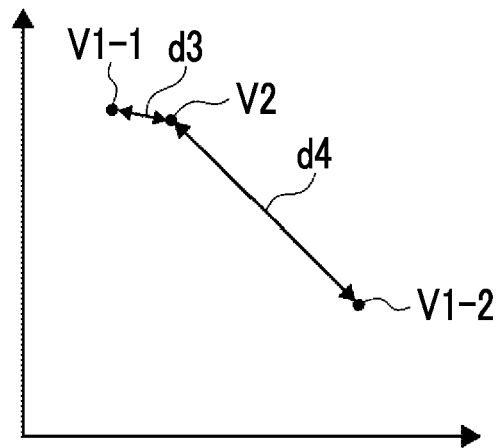
FIG. 13 is a diagram for describing specifying of a first feature amount.

The specifying unit 35 derives the distance between the first feature amount V1 derived by the first analysis unit 32 and the second feature amount V2 derived by the second analysis unit 34 in the feature space. Moreover, the first feature amount V1 corresponding to the second feature amount V2 is specified based on the derived distance. FIG. 13 is a diagram for describing specifying of the first feature amount. It should be noted that, in FIG. 13, the feature space is shown in two dimensions for the sake of description. As shown in FIG. 13, in a case in which a distance d3 between the first feature amount V1-1 and the second feature amount V2 is compared with a distance d4 between the first feature amount V1-2 and the second feature amount V2 in the feature space, d3<d4. Therefore, the specifying unit 35 specifies the first feature amount corresponding to the second feature amount V2 as the first feature amount V1-1.

Figure 14:
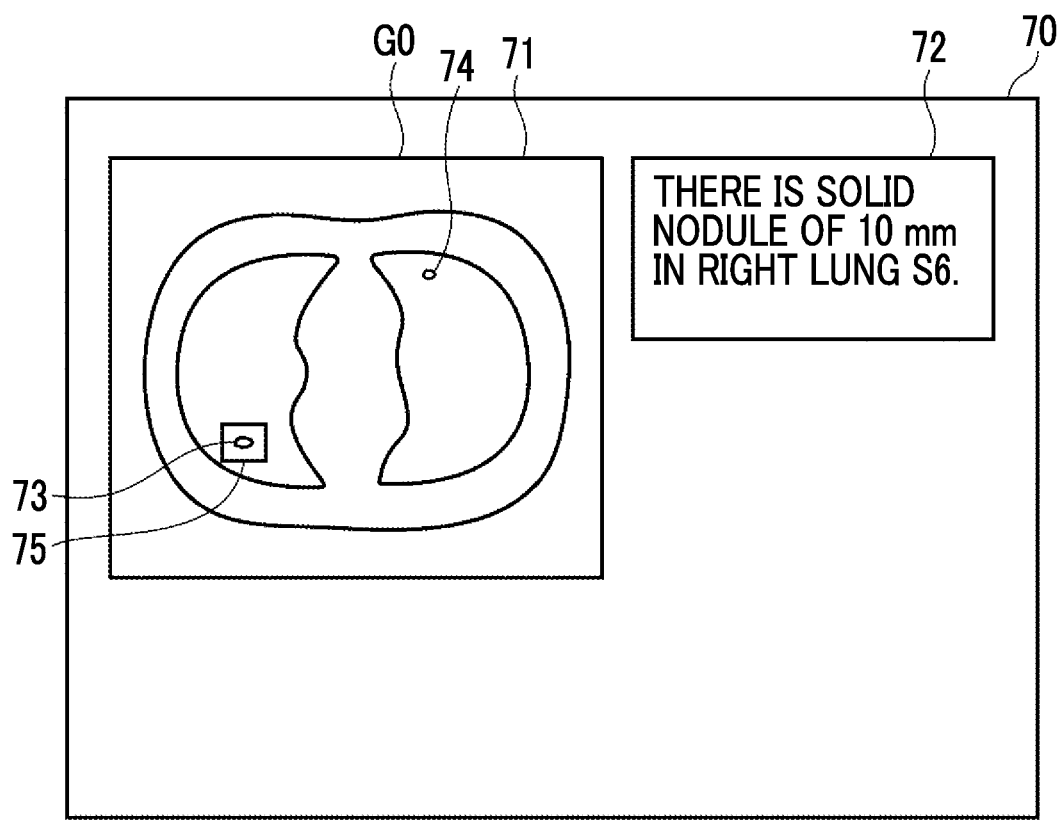
FIG. 14 is a diagram showing a display screen.

The display controller 36 displays the object from which the specified first feature amount is derived, in distinction from other regions in the target medical image G0. FIG. 14 is a diagram showing a creation screen of the interpretation report displayed on the interpretation WS 3. As shown in FIG. 14, a creation screen 70 of the interpretation report includes an image display region 71 and a sentence display region 72. The target medical image G0 is displayed in the image display region 71. In FIG. 14, the target medical image G0 is one tomographic image constituting the three-dimensional image of the chest. The opinion sentence input by the interpreter is displayed in the sentence display region 72. In FIG. 14, the opinion sentence of "There is the solid nodule of 10 mm in the right lung S6." is displayed. It should be noted that the right lung S6 is synonymous with the right lung lower lobe S6.

The target medical image G0 shown in FIG. 14 includes a lesion 73 in the right lung and a lesion 74 in the left lung. In a case in which the first feature amount V1-1 derived for the lesion 73 of the right lung is compared with the first feature amount V1-2 derived for the lesion 74 of the left lung, the distance from the second feature amount V2 derived for the opinion sentence of "There is the solid nodule of 10 mm in the right lung S6." is smaller in the first feature amount V1-1. Therefore, the display controller 36 displays the lesion 73 of the right lung in distinction from other regions in the target medical image G0. In FIG. 14, by surrounding the lesion 73 of the right lung by a rectangular mark 75, the lesion 73 is displayed in distinction from other regions, but the present disclosure is not limited to this. A mark of any shape, such as an arrow, can be used.

Figure 15:
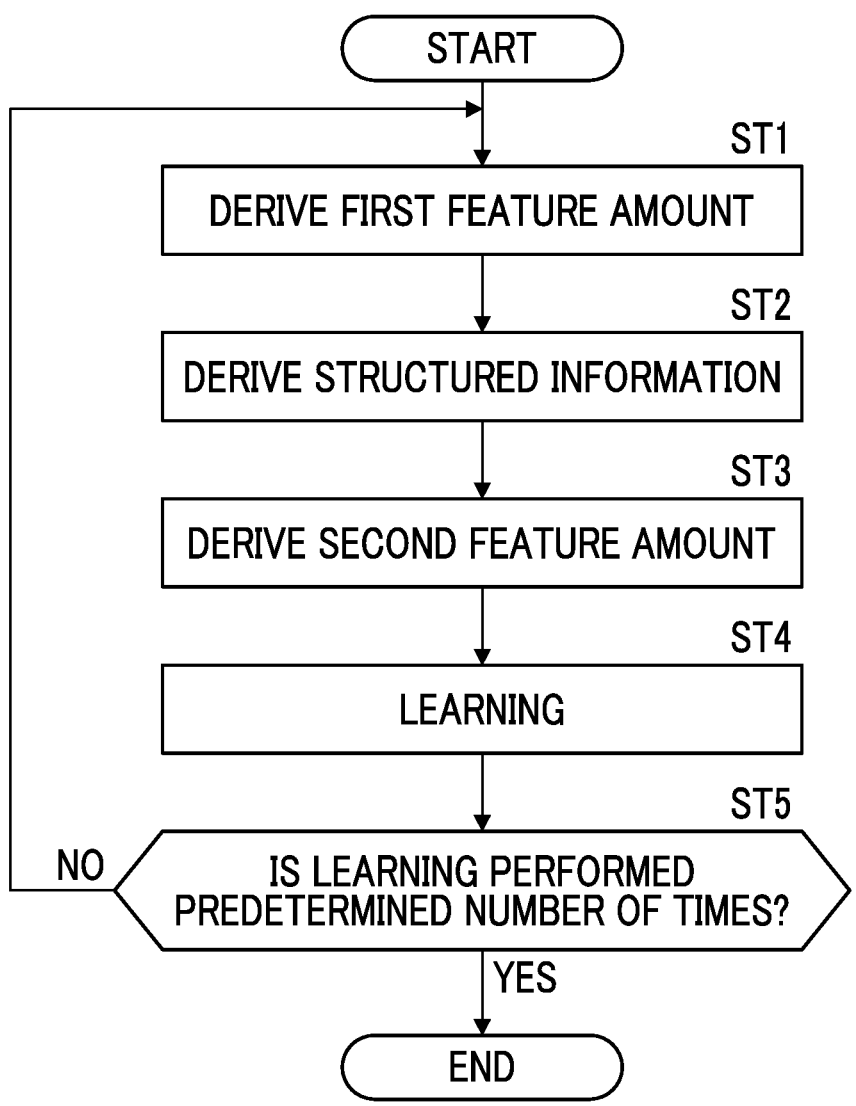
FIG. 15 is a flowchart showing learning processing performed in the first embodiment.

Then, processing performed in the first embodiment will be described. FIG. 15 is a flowchart of learning processing according to the first embodiment. It should be noted that, the image and the interpretation report used in learning are acquired from the image server 5 and the report server 6 by the information acquisition unit 21, respectively, and stored in the storage 13. In addition, a learning end condition is that learning is performed a predetermined number of times.

First, the first derivation unit 22 derives the first feature amount V1 for the object included in the image by the first neural network 61 (step ST1). In addition, the structured information derivation unit 23 derives the structured information from the sentence including the description of the object (step ST2). Subsequently, the second derivation unit 24 derives the second feature amount V2 for the sentence including the description of the object from the structured information by the second neural network 62 (step ST3). It should be noted that the processing of steps ST2 and ST3 may be performed first, or the processing of step ST1, and steps ST2 and ST3 may be performed in parallel.

Next, the learning unit 25 trains the first neural network and the second neural network such that the distance between the derived first feature amount V1 and second feature amount V2 is reduced in accordance with the correspondence relationship between the image and the sentence (step ST4). Further, the learning unit 25 determines whether or not learning has been performed a predetermined number of times (learning of a predetermined number of times: step ST5), and in a case in which a negative determination is made in step ST5, the learning unit 25 returns to step ST1 and repeats the processing of step ST1 to step ST5. In a case in which a positive determination is made in step ST5, the processing ends.

Figure 16:
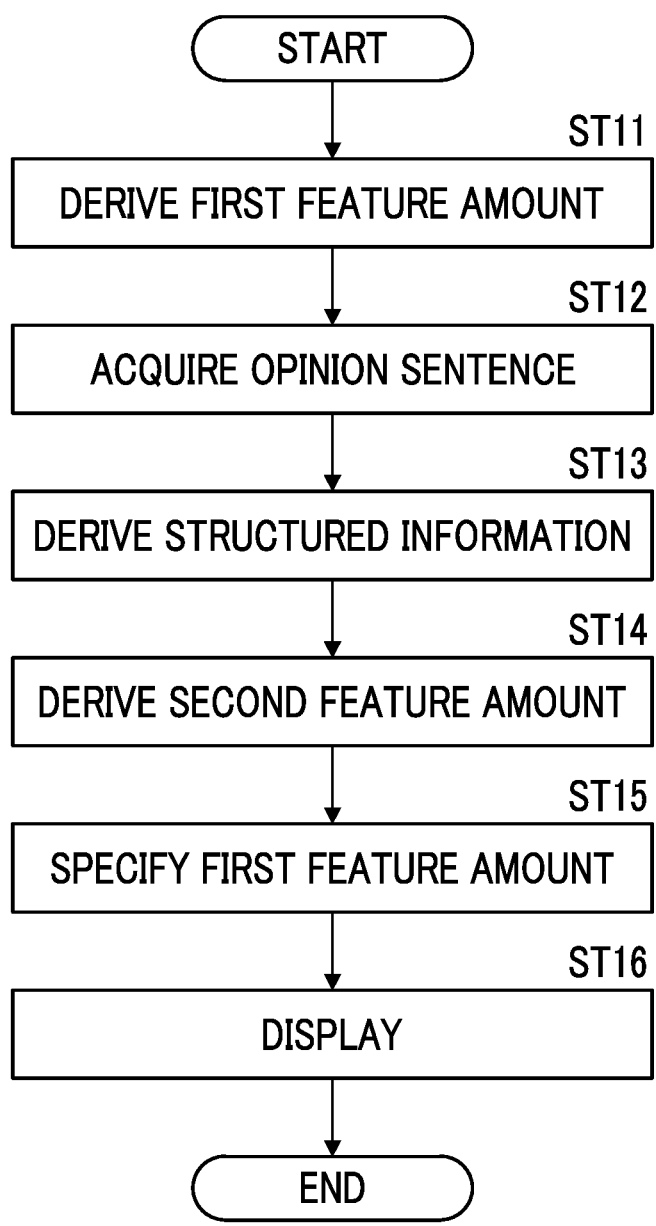
FIG. 16 is a flowchart showing information processing performed in the first embodiment.

Then, information processing according to the first embodiment will be described. FIG. 16 is a flowchart of the information processing according to the first embodiment. It should be noted that, the target medical image G0, which is a processing target, is acquired by the information acquisition unit 31 and stored in the storage 43. First, the first analysis unit 32 analyzes the target medical image G0 using the first derivation model 32A to derive the first feature amount V1 for the object, such as the lesion, included in the target medical image G0 (step ST11).

Next, the information acquisition unit 31 acquires the opinion sentence input by the interpreter by using the input device 45 (step ST12), and the structured information derivation unit 33 derives the structured information from the input opinion sentence (step ST13). Next, the second analysis unit 34 analyzes the derived structured information by using the second derivation model 34A to derive the second feature amount V2 for the input opinion sentence (step ST14).

Subsequently, the specifying unit 35 derives the distance between the first feature amount V1 derived by the first analysis unit 32 and the second feature amount V2 derived by the second analysis unit 34 in the feature space, and specifies the first feature amount V1 corresponding to the second feature amount V2 based on the derived distance (step ST15). Moreover, the display controller 36 displays the object from which the specified first feature amount V1 is derived, in distinction from other regions in the target medical image G0 (step ST16), and the processing ends.

In this way, in the learning device according to the first embodiment, the structured information about the sentence is derived by structuring the sentence including the description of the object included in the image, and the second feature amount V2 for the sentence is derived from the structured information. As described above, the first derivation model 32A and the second derivation model 34A are constructed by training the first neural network 61 and the second neural network 62 such that, in the feature space to which the first feature amount V1 and the second feature amount V2 belong, the distance between the derived first feature amount V1 and second feature amount V2 is reduced in a case in which the object included in the image and the object described in the sentence correspond to each other.

Therefore, even in a case in which there are variations in the expressions in the sentences for training the second neural network 62, substantially the same structured information will be derived in a case in which the contents are the same. In particular, in a case in which the structured information is normalized, the same structured information will be derived. As a result, since the second neural network 62 is trained using substantially the same unique expression, the second derivation model 34A can be constructed to derive the second feature amount without being affected by the variation in the expression. Therefore, in a case in which a large number of the sentences for training the second neural network 62 are not prepared, the first derivation model 32A and the second derivation model 34A which can associate the image with the sentence with high accuracy can be constructed.

In addition, by applying the first derivation model 32A and the second derivation model 34A constructed by learning to the information processing apparatus 30 according to the first embodiment, the first feature amount V1 and the second feature amount V2 are derived such that, even in a case in which there are variations in the expressions of the input sentences, the image including the corresponding object and the sentence including the description of the object are associated with each other, and the medical image including non-corresponding object and the sentence including the description of the object are not associated with each other. Therefore, by using the derived first feature amount V1 and second feature amount V2 it is possible to accurately associate the image with the sentence.

In addition, since it is possible to accurately associate the image with the sentence, it is possible to accurately specify the object described in the input opinion sentence in the medical image in a case of creating the interpretation report for the medical image.

It should be noted that, in the learning device according to the first embodiment, the second derivation unit may be constructed by further using the relationship included in the structured information. In the following, this case will be described as a second embodiment of the learning device. It should be noted that, a configuration of the learning device according to the second embodiment is the same as the configuration of the learning device 7 shown in FIG. 4 except that the second feature amount is derived by the second derivation unit 24 using a second neural network including a graph convolutional network (hereinafter, referred to as a GCN) instead of the second neural network 62, and thus the detailed description of the device will be omitted here.

Figure 17:
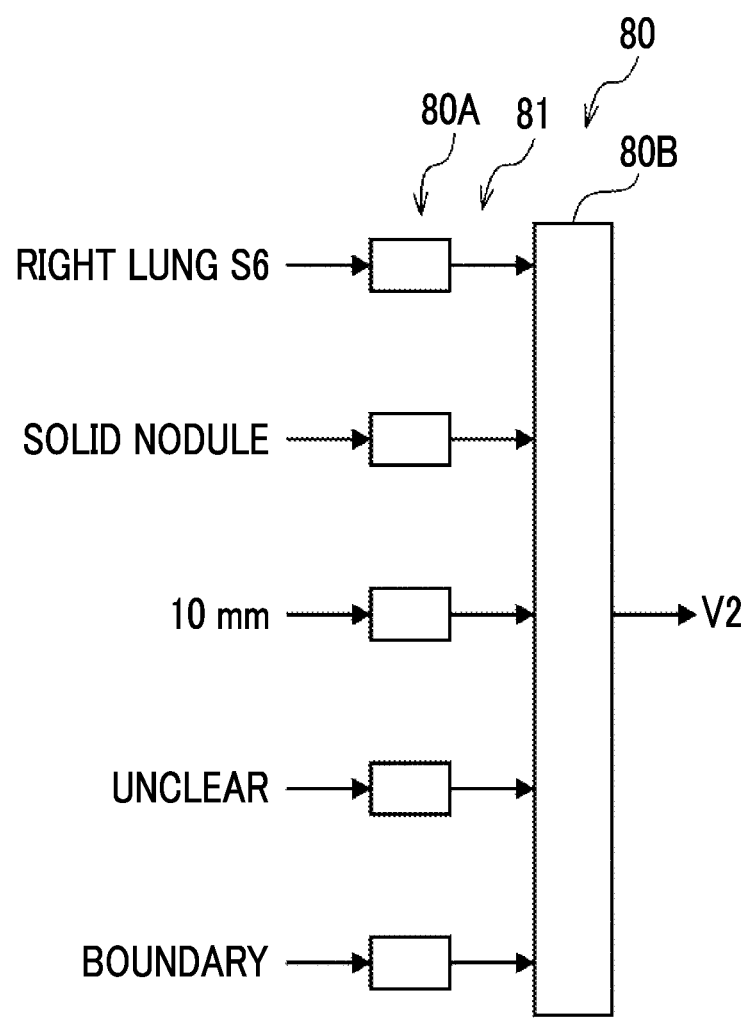
FIG. 17 is a diagram schematically showing a second neural network trained by a learning device according to a second embodiment.

FIG. 17 is a diagram schematically showing the second neural network trained by the learning device according to the second embodiment. As shown in FIG. 17, a second neural network 80 according to the second embodiment includes an embedding layer 80A and a GCN 80B. In the second embodiment, the second derivation unit 24 inputs the input structured information before normalization to the embedding layer 80A. The embedding layer 80A outputs a feature vector 81 for the structured information. The GCN 80B derives the second feature amount V2 based on the feature vector 81 and the relationship derived by the structured information derivation unit 23.

Figure 18:
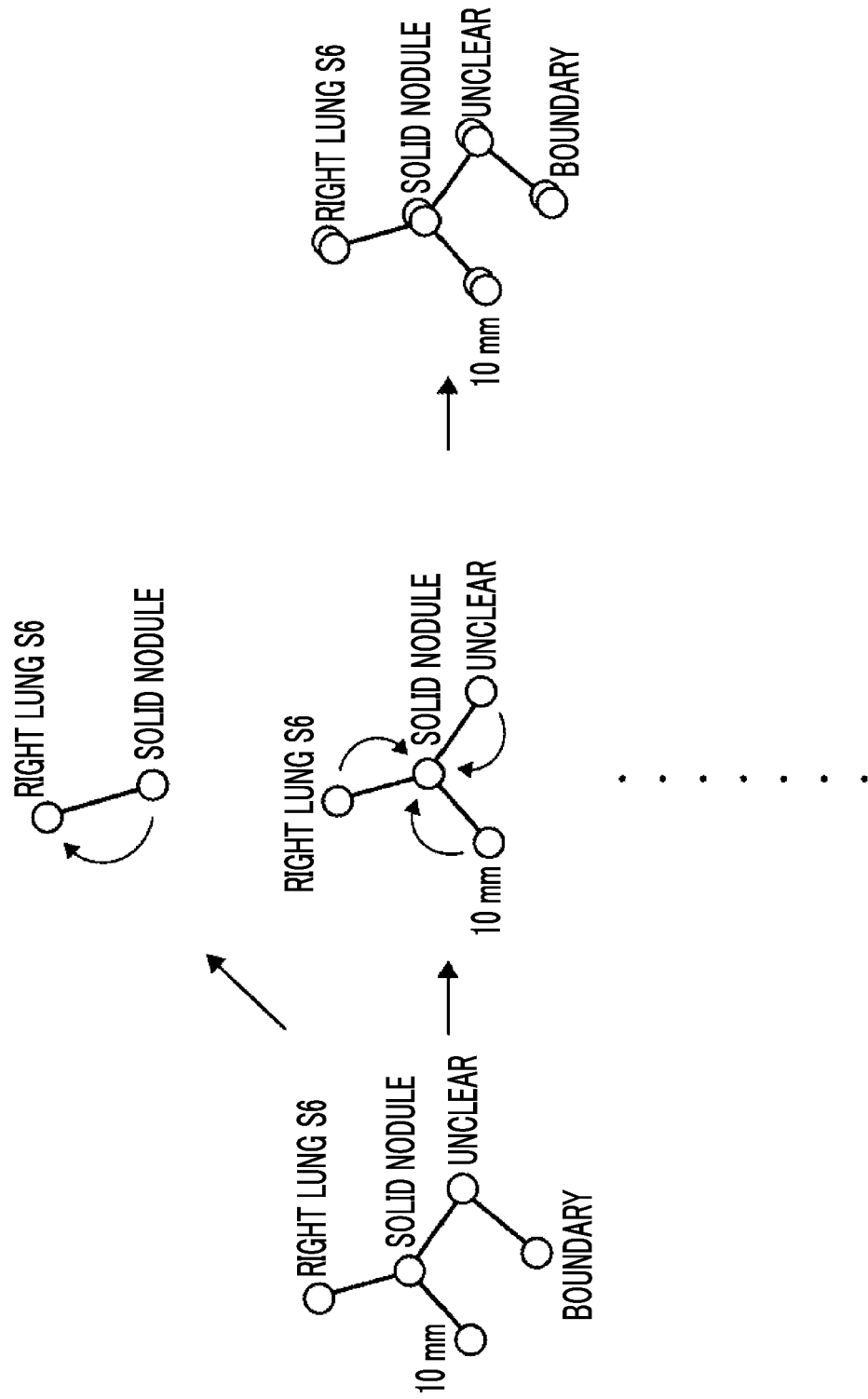
FIG. 18 is a diagram for describing the derivation of a second feature amount by a GCN.

FIG. 18 is a diagram for describing the derivation of the second feature amount by the GCN. In FIG. 18, the structured information before normalization is shown in a graph structure based on the relationship derived by the structured information derivation unit 23. That is, a state is shown in which a node of the unique expression of "solid nodule (opinion+)" that represents the opinion is related to a node of the unique expression of "10 mm (size)" that represents the size, a node of the unique expression of "right lung S6 (position)" that represents the position, and a node of the unique expression of "unclear (opinion+)" that represents the opinion, but is not related to a node of the unique expression of "boundary (position)" that represents the position, and the node of the unique expression of "boundary (position)" that represents the position is related to the node of the unique expression of "unclear (opinion+)" that represents the opinion. It should be noted that, in FIG. 18, "solid nodule (opinion+)", "10 mm (size)", "right lung S6 (position)", "unclear (opinion+)", and "boundary (position)" are shown as "solid nodule", "10 mm", "right lung S6", "unclear", and "boundary".

In the GCN 80B, in each node, the feature vector of its own node and the feature vector of the adjacent node are convolved, and the feature vector of each node is updated. Moreover, the convolution using the updated feature vector is repeatedly performed, and the feature vector for the solid nodule that represents the characteristic of the typical lesion in the structured information is output as the second feature amount V2.

In the second embodiment, the learning unit 25 trains the first neural network 61 and the second neural network 80 using the first feature amount V1 and the second feature amount V2 as in the first embodiment. As a result, in the second embodiment, the second feature amount V2 can be derived also in consideration of the relationship of the unique expression derived from the sentence.

Figure 19:
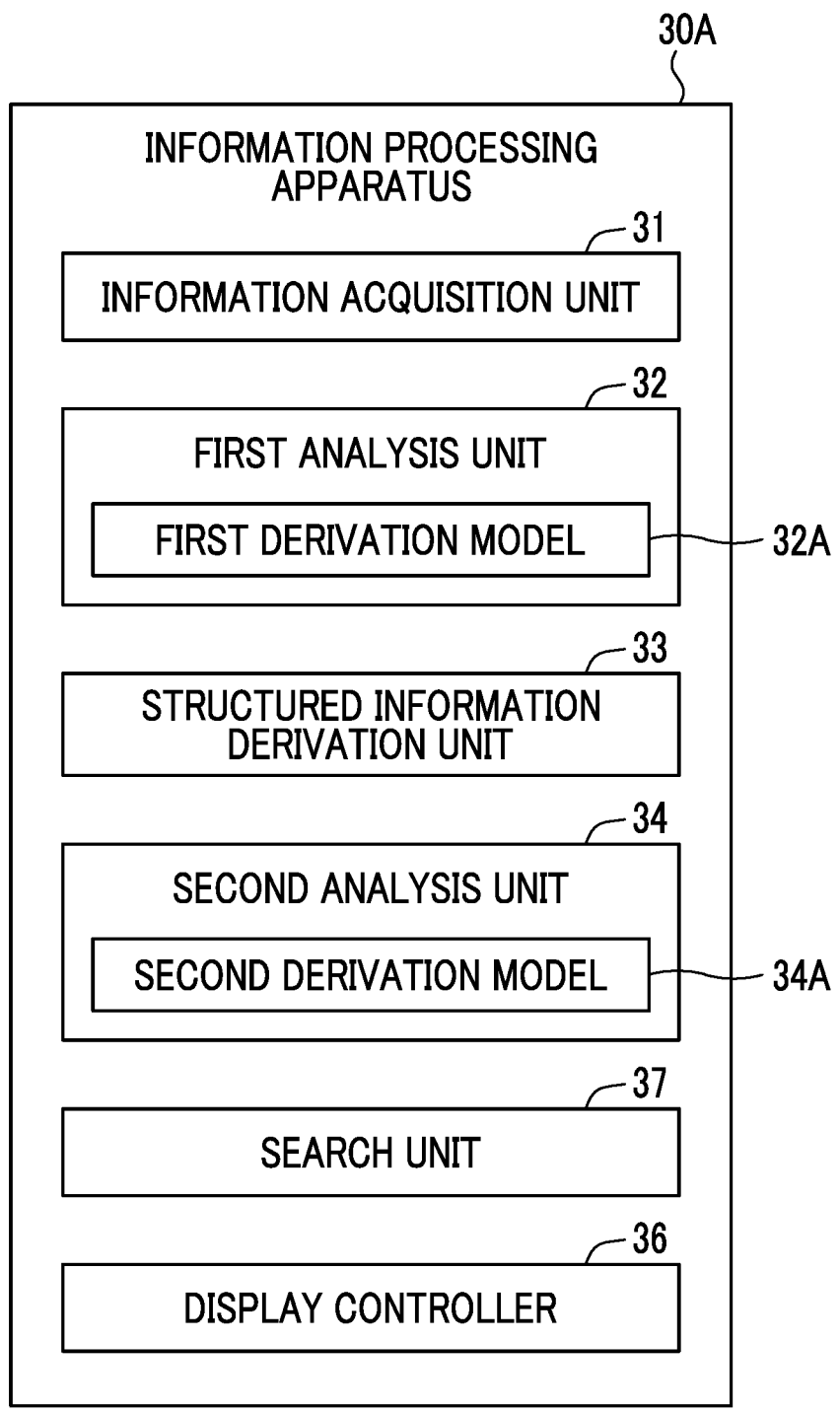
FIG. 19 is a functional configuration diagram of an information processing apparatus according to the second embodiment.

Then, the second embodiment of the information processing apparatus will be described. FIG. 19 is a functional configuration diagram of the information processing apparatus according to the second embodiment. It should be noted that, in FIG. 19, the same configurations as those in FIG. 11 are denoted by the same reference numerals, and the detailed description thereof will be omitted. As shown in FIG. 19, an information processing apparatus 30A according to the second embodiment is different from the information processing apparatus according to the first embodiment in that a search unit 37 is provided instead of the specifying unit 35.

In the information processing apparatus 30A according to the second embodiment, the information acquisition unit 31 acquires a large number of medical images stored in the image server 5. Moreover, the first analysis unit 32 derives the first feature amount V1 for each of the medical images. The information acquisition unit 31 transmits the first feature amount V1 to the image server 5. In the image server 5, the medical image is stored in the image DB 5A in association with the first feature amount V1. The medical image registered in the image DB 5A in association with the first feature amount V1 is referred to as a reference image in the following description.

In addition, in the information processing apparatus 30A according to the second embodiment, the interpretation report is generated by the interpreter interpreting the target medical image G0 in the interpretation WS 3 and inputting the opinion sentence including the interpretation result by using the input device 45. The structured information derivation unit 33 derives the structured information from the input opinion sentence. The derivation of the structured information is performed in the same manner as in the structured information derivation unit 23 of the learning device 7. The second analysis unit 34 derives the second feature amount V2 for the input opinion sentence by analyzing the derived structured information using the second derivation model 34A constructed by the learning device 7 described above.

Figure 20:
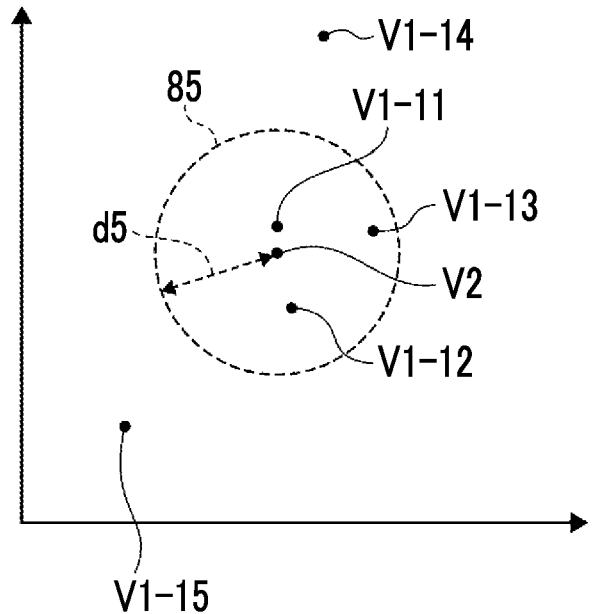
FIG. 20 is a diagram for describing a search.

The search unit 37 refers to the image DB 5A to search for the reference image associated with the first feature amount V1 having a small distance from the second feature amount V2 derived by the second analysis unit 34 in the feature space. FIG. 20 is a diagram for describing the search performed in the information processing apparatus 30A according to the second embodiment. It should be noted that, also in FIG. 20, the feature space is shown in two dimensions for the sake of description. In addition, for the sake of description, five first feature amounts V1-11 to V1-15 are plotted in the feature space.

The search unit 37 specifies the first feature amount having the distance from the second feature amount V2 within a predetermined threshold value in the feature space. In FIG. 20, a circle 85 having a radius d5 centered on the second feature amount V2 is shown. The search unit 37 specifies the first feature amount included in the circle 85 in the feature space. In FIG. 20, three first feature amounts V1-11 to V1-13 are specified.

The search unit 37 searches the image DB 5A for the reference image associated with the specified first feature amounts V1-11 to V1-13, and acquires the searched reference image from the image server 5.

Figure 21:
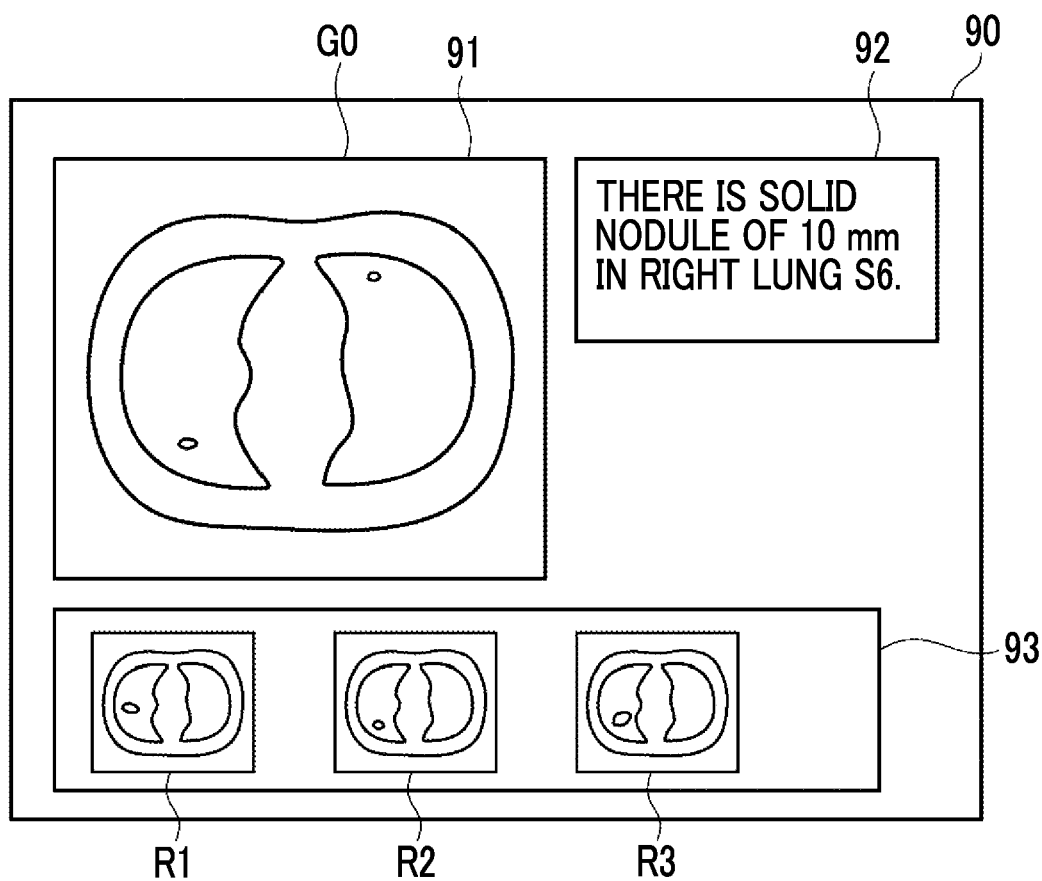
FIG. 21 is a diagram showing the display screen.

The display controller 36 displays the acquired reference image on the display 44. FIG. 21 is a diagram showing a creation screen of the interpretation report in the information processing apparatus 30A according to the second embodiment. As shown in FIG. 21, a creation screen 90 includes an image display region 91, a sentence display region 92, and a result display region 93. The target medical image G0 is displayed in the image display region 91. In FIG. 21, the target medical image G0 is one tomographic image constituting the three-dimensional image of the chest. The opinion sentence input by the interpreter is displayed in the sentence display region 92. In FIG. 21, the opinion sentence of "There is the solid nodule of 10 mm in the right lung S6." is displayed.

The reference image searched by the search unit 37 is displayed in the result display region 93. In FIG. 21, three reference images R1 to R3 are displayed in the result display region 93.

Figure 22:
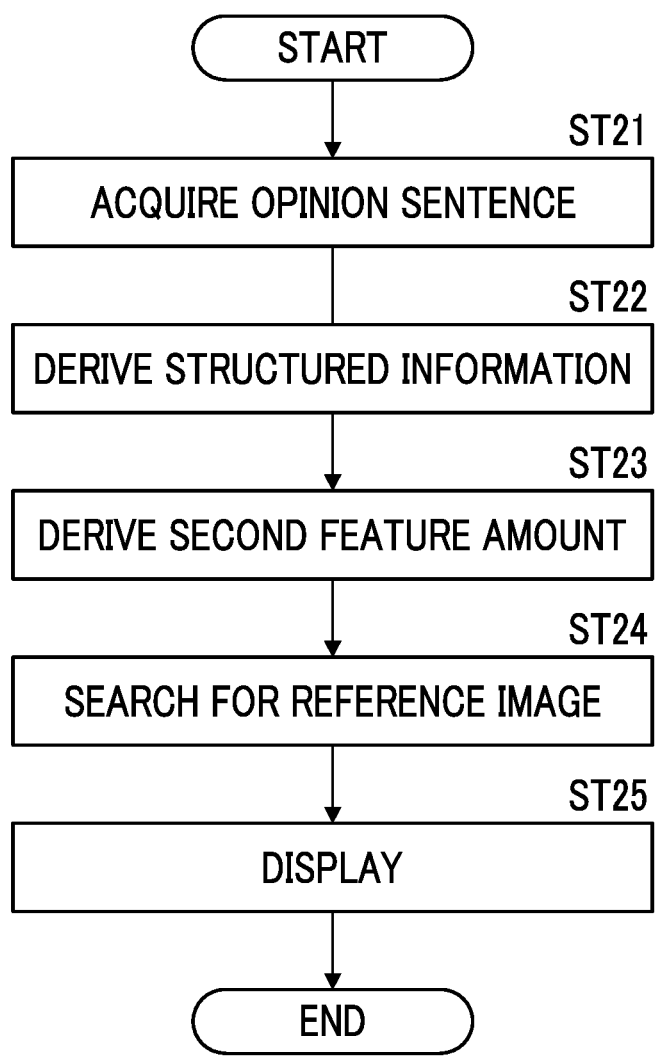
FIG. 22 is a flowchart showing information processing performed in the second embodiment.

Then, information processing according to the second embodiment will be described. FIG. 22 is a flowchart of the information processing according to the second embodiment. It should be noted that, the first feature amount of the reference image is derived by the first analysis unit 32, and a larger number of the first feature amounts are registered in the image DB 5A in association with the reference image. In addition, the target medical image G0 is displayed on the display 44 by the display controller 36. In the second embodiment, the information acquisition unit 31 acquires the opinion sentence input by the interpreter by using the input device 45 (step ST21), and the structured information derivation unit 33 derives the structured information from the input opinion sentence (step ST22). Next, the second analysis unit 34 analyzes the derived structured information by using the second derivation model 34A to derive the second feature amount V2 for the input opinion sentence (step ST23).

Subsequently, the search unit 37 refers to the image DB 5A and searches for the reference image associated with the first feature amount V1 having a small distance from the second feature amount V2 (step ST24). Moreover, the display controller 36 displays the searched reference image on the display 44 (step ST25), and the processing ends.

The reference images R1 to R3 searched in the second embodiment are the medical images having similar features to the opinion sentences input by the interpreter. Since the opinion sentences relate to the target medical image G0, the reference images R1 to R3 have similar cases to the target medical image G0. Therefore, according to the second embodiment, it is possible to interpret the target medical image G0 with reference to the reference image having a similar case. In addition, the interpretation report for the reference image can be acquired from the report server 6 and used to create the interpretation report for the target medical image G0.

It should be noted that, in the first embodiment of the information processing apparatus, in a case in which the display controller 36 displays the opinion sentence, a notification of the unique expression that contributes to the association with the first feature amount for the object included in the image may be given. In this case, the second derivation unit 24 constructed from the second neural network 62 having a network structure in which the RNN and the attention mechanism shown in FIG. 10 described above are combined need only be used to specify the unique expression that contributes to the association with the first feature amount in accordance with the magnitude of weighting in the attention mechanism. In addition, the degree of contribution may be derived in accordance with the magnitude of the weighting coefficient.

Figure 23:
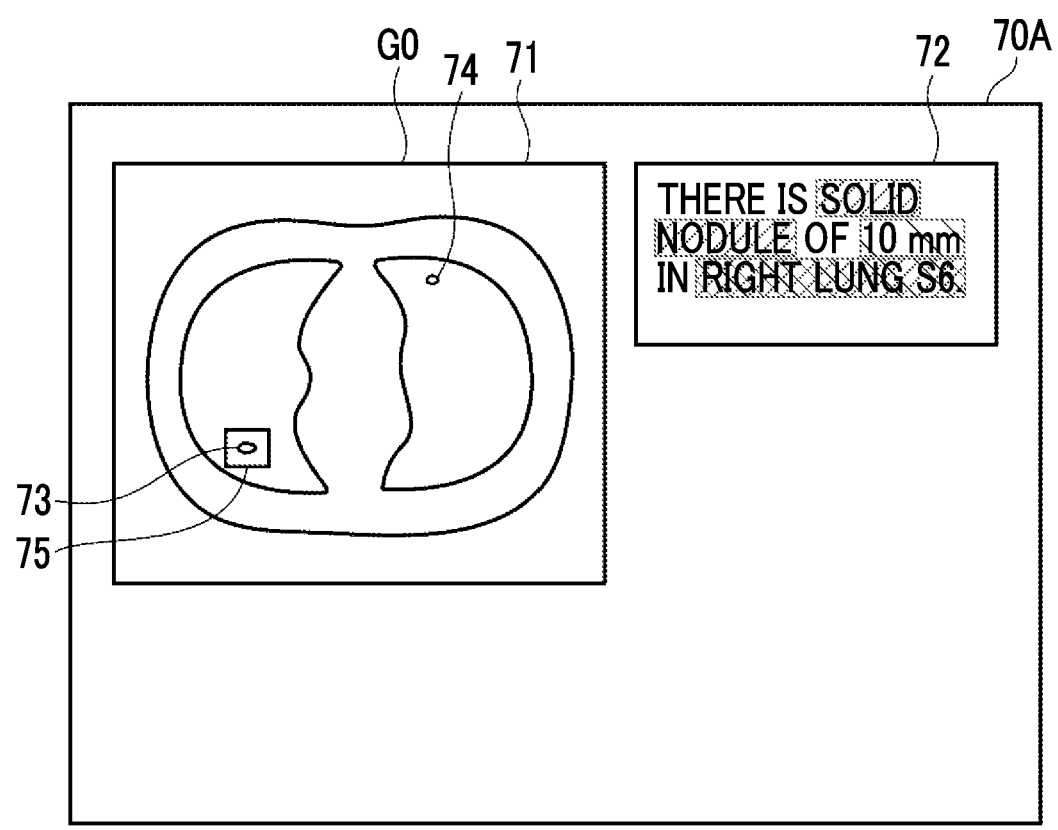
FIG. 23 is a diagram showing another example of a creation screen of the interpretation report displayed on an interpretation WS.

FIG. 23 is a diagram showing another example of the creation screen of the interpretation report displayed on the interpretation WS 3. In a creation screen 70A of the interpretation report shown in FIG. 23, "right lung S6", "10 mm", and "solid nodule" included in the opinion sentence of "There is a solid nodule of 10 mm in the right lung S6." displayed in the sentence display region 72 are the unique expressions that contribute to the association with the first feature amount for the lesion 73 included in the target medical image G0, and these unique expressions are highlighted. It should be noted that, in FIG. 23, it is shown that the degree of contribution of each unique expression is different by a difference in an interval of a hatching lines and the number of lines. In FIG. 23, the unique expressions included in the opinion sentences are in the order of "right lung S6", "solid nodule", and "10 mm" in descending order of the degree of contribution. In this way, by giving the notification of the unique expression that contributes to the association with the first feature amount, an important keyword in the opinion sentence can be easily recognized.

It should be noted that, of course, the notification of the unique expression that contributes to the association with the first feature amount may be given on the creation screen 90 shown in FIG. 21 in the second embodiment of the information processing apparatus.

In addition, in the embodiments described above, the derivation model that derives the feature amounts of the medical image and the opinion sentence of the medical image is constructed, but the present disclosure is not limited to this. For example, it is needless to say that the technology of the present disclosure can be applied to a case of constructing a derivation model that derives feature amounts of a photographic image and a sentence, such as a comment, corresponding to the photographic image.

In addition, in the embodiments described above, for example, as the hardware structure of the processing unit that executes various types of processing, such as the information acquisition unit 21, the first derivation unit 22, the structured information derivation unit 23, the second derivation unit 24, and the learning unit 25 of the learning device 7, and the information acquisition unit 31, the first analysis unit 32, the structured information derivation unit 33, the second analysis unit 34, the specifying unit 35, the display controller 36, and the search unit 37 of the information processing apparatuses 30 and 30A, the following various processors can be used. As described above, the various processors include, in addition to the CPU which is a general-purpose processor that executes the software (program) to function as the various processing units described above, a programmable logic device (PLD), which is a processor of which a circuit configuration can be changed after manufacturing, such as a field programmable gate array (FPGA), a dedicated electric circuit, which is a processor having a circuit configuration specially designed to execute specific processing, such as an application specific integrated circuit (ASIC), and the like.

One processing unit may be composed of one of the various processors, or may be composed of a combination of two or more processors of the same type or different types (for example, a combination of a plurality of FPGAs or a combination of a CPU and an FPGA). In addition, a plurality of processing units may be composed of one processor. A first example of a configuration in which the plurality of processing units are composed of one processor includes a form in which one processor is composed of a combination of one or more CPUs and software and the processor functions as the plurality of processing units, as represented by the computer, such as a client and a server. A second example thereof includes a form in which a processor that realizes the function of the entire system including the plurality of processing units by one integrated circuit (IC) chip is used, as represented by a system on chip (SoC) or the like. In this way, the various processing units are composed of one or more of the various processors as the hardware structure.

Further, as the hardware structure of the various processors, more specifically, an electric circuit (circuitry) in which circuit elements, such as semiconductor elements, are combined can be used.

What is claimed is:

1. A learning device comprising:
at least one processor,
wherein the processor
    derives a first feature amount for an object included in an image by a first neural network,
    structures a sentence including description of the object included in the image to derive structured information for the sentence,
    derives a second feature amount for the sentence from the structured information by a second neural network, and
    constructs a first derivation model that derives a feature amount for the object included in the image and a second derivation model that derives a feature amount for the sentence including the description of the object by training the first neural network and the second neural network such that, in a feature space to which the first feature amount and the second feature amount belong, a distance between the derived first feature amount and second feature amount is smaller in a case in which the object included in the image and the object described in the sentence correspond to each other than a case in which the object included in the image and the object described in the sentence do not correspond to each other.

2. The learning device according to claim 1,
wherein the processor trains the first neural network and the second neural network such that, in the feature space, the distance between the derived first feature amount and second feature amount is larger in a case in which the object included in the image and the object described in the sentence do not correspond to each other than a case in which the object included in the image and the object described in the sentence correspond to each other.

3. The learning device according to claim 1,
wherein the processor extracts one or more unique expressions for the object from the sentence and determines factuality for the unique expression to derive the unique expression and a determination result of the factuality as the structured information.

4. The learning device according to claim 3, wherein the unique expression represents at least one of a position, an opinion, or a size of the object, and the determination result of the factuality represents any of positivity, negativity, or suspicion for the opinion.

5. The learning device according to claim 3, wherein, in a case in which a plurality of the unique expressions are extracted, the processor further derives a relationship between the unique expressions as the structured information.

6. The learning device according to claim 5, wherein the relationship represents whether or not the plurality of unique expressions are related to each other.

7. The learning device according to claim 3, wherein the processor normalizes the unique expression and the factuality to derive normalized structured information.

8. The learning device according to claim 1, wherein the image is a medical image, the object included in the image is a lesion included in the medical image, and the sentence is an opinion sentence in which an opinion about the lesion is described.

9. An information processing apparatus comprising:
at least one processor,
wherein the processor
derives a first feature amount for one or more objects included in a target image by the first derivation model constructed by the learning device according to claim 1,
structures one or more target sentences including description of the object to derive structured information for the target sentence,
derives a second feature amount for the target sentence from the structured information for the target sentence by the second derivation model constructed by the learning device according to claim 1,
specifies the first feature amount corresponding to the second feature amount based on a distance between the derived first feature amount and second feature amount in a feature space, and
displays the object from which the specified first feature amount is derived, in distinction from other regions in the target image.

10. An information processing apparatus comprising:
at least one processor,
wherein the processor
receives input of a target sentence including description of an object,
structures the target sentence to derive structured information for the target sentence,
derives a second feature amount for the input target sentence from the structured information for the target sentence by the second derivation model constructed by the learning device according to claim 1,
refers to a database in which a first feature amount for one or more objects included in a plurality of reference images, which is derived by the first derivation model constructed by the learning device according to claim 1, is associated with each of the reference images, to specify at least one first feature amount corresponding to the second feature amount based on a distance between the first feature amounts for the plurality of reference images and the derived second feature amount in a feature space, and
specifies the reference image associated with the specified first feature amount.

11. The information processing apparatus according to claim 9,
wherein the processor gives a notification of a unique expression that contributes to association with the first feature amount.

12. A learning method comprising:
deriving a first feature amount for an object included in an image by a first neural network;
structuring a sentence including description of the object included in the image to derive structured information for the sentence;
deriving a second feature amount for the sentence from the structured information by a second neural network; and
constructing a first derivation model that derives a feature amount for the object included in the image and a second derivation model that derives a feature amount for the sentence including the description of the object by training the first neural network and the second neural network such that, in a feature space to which the first feature amount and the second feature amount belong, a distance between the derived first feature amount and second feature amount is smaller in a case in which the object included in the image and the object described in the sentence correspond to each other than a case in which the object included in the image and the object described in the sentence do not correspond to each other.

13. An information processing method comprising:
deriving a first feature amount for one or more objects included in a target image by the first derivation model constructed by the learning device according to claim 1;
structuring one or more target sentences including description of the object to derive structured information for the target sentence;
deriving a second feature amount for the target sentence from the structured information for the target sentence by the second derivation model constructed by the learning device according to claim 1;
specifying the first feature amount corresponding to the second feature amount based on a distance between the derived first feature amount and second feature amount in a feature space; and
displaying the object from which the specified first feature amount is derived, in distinction from other regions in the target image.

14. An information processing method comprising:
receiving input of a target sentence including description of an object;
structuring the target sentence to derive structured information for the target sentence;
deriving a second feature amount for the input target sentence from the structured information for the target sentence by the second derivation model constructed by the learning device according to claim 1;
referring to a database in which a first feature amount for one or more objects included in a plurality of reference images, which is derived by the first derivation model constructed by the learning device according to claim 1, is associated with each of the reference images, to specify at least one first feature amount corresponding to the second feature amount based on a distance between the first feature amounts for the plurality of reference images and the derived second feature amount in a feature space; and specifying the reference image associated with the specified first feature amount.

15. A non-transitory computer-readable storage medium that stores a learning program causing a computer to execute:

a procedure of deriving a first feature amount for an object included in an image by a first neural network;

a procedure of structuring a sentence including description of the object included in the image to derive structured information for the sentence;

a procedure of deriving a second feature amount for the sentence from the structured information by a second neural network; and a procedure of constructing a first derivation model that derives a feature amount for the object included in the image and a second derivation model that derives a feature amount for the sentence including the description of the object by training the first neural network and the second neural network such that, in a feature space to which the first feature amount and the second feature amount belong, a distance between the derived first feature amount and second feature amount is smaller in a case in which the object included in the image and the object described in the sentence correspond to each other than a case in which the object included in the image and the object described in the sentence do not correspond to each other.

16. A non-transitory computer-readable storage medium that stores an information processing program causing a computer to execute:

a procedure of deriving a first feature amount for one or more objects included in a target image by the first derivation model constructed by the learning device according to claim 1;

a procedure of structuring one or more target sentences including description of the object to derive structured information for the target sentence;

a procedure of deriving a second feature amount for the target sentence from the structured information for the target sentence by the second derivation model constructed by the learning device according to claim 1;

a procedure of specifying the first feature amount corresponding to the second feature amount based on a distance between the derived first feature amount and second feature amount in a feature space; and a procedure of displaying the object from which the specified first feature amount is derived, in distinction from other regions in the target image.

17. A non-transitory computer-readable storage medium that stores an information processing program causing a computer to execute:

a procedure of receiving input of a target sentence including description of an object;

a procedure of structuring the target sentence to derive structured information for the target sentence;

a procedure of deriving a second feature amount for the input target sentence from the structured information for the target sentence by the second derivation model constructed by the learning device according to claim 1;

a procedure of referring to a database in which a first feature amount for one or more objects included in a plurality of reference images, which is derived by the first derivation model constructed by the learning device according to claim 1, is associated with each of the reference images, to specify at least one first feature amount corresponding to the second feature amount based on a distance between the first feature amounts for the plurality of reference images and the derived second feature amount in a feature space; and a procedure of specifying the reference image associated with the specified first feature amount.

* * * * *